US008518701B2

(12) United States Patent
Fahrenkrug et al.

(10) Patent No.: US 8,518,701 B2
(45) Date of Patent: Aug. 27, 2013

(54) METHODS AND MATERIALS FOR PRODUCING TRANSGENIC ARTIODACTYLS

(75) Inventors: Scott C. Fahrenkrug, Minneapolis, MN (US); Daniel F. Carlson, Inner Grove Heights, MN (US)

(73) Assignee: Recombinetics, Inc., Minneapolis, MN (US)

( * ) Notice: Subject to any disclaimer, the term of this patent is extended or adjusted under 35 U.S.C. 154(b) by 0 days.

(21) Appl. No.: 13/467,588

(22) Filed: May 9, 2012

(65) Prior Publication Data

US 2012/0220037 A1 Aug. 30, 2012

Related U.S. Application Data

(63) Continuation of application No. 13/025,373, filed on Feb. 11, 2011.

(60) Provisional application No. 61/303,523, filed on Feb. 11, 2010, provisional application No. 61/309,949, filed on Mar. 3, 2010.

(51) Int. Cl.
C12N 5/16 (2006.01)
C12N 5/07 (2010.01)
C12N 15/63 (2006.01)

(52) U.S. Cl.
USPC .......................................... 435/455; 435/347

(58) Field of Classification Search
USPC ................................................. 435/455, 347
See application file for complete search history.

(56) References Cited

U.S. PATENT DOCUMENTS

| 4,873,191 | A | 10/1989 | Wagner et al. |
|---|---|---|---|
| 5,239,060 | A | 8/1993 | Kunkel et al. |
| 5,430,129 | A | 7/1995 | Campbell et al. |
| 5,521,071 | A | 5/1996 | Attie et al. |
| 5,610,053 | A | 3/1997 | Chung et al. |
| 5,731,178 | A | 3/1998 | Sippel et al. |
| 5,798,209 | A | 8/1998 | Chan |
| 5,985,846 | A | 11/1999 | Kochanek et al. |
| 6,100,448 | A | 8/2000 | Thompson et al. |
| 6,174,527 | B1 | 1/2001 | Wilson et al. |
| 6,395,549 | B1 | 5/2002 | Tuan et al. |
| 6,548,741 | B2 | 4/2003 | DeSousa et al. |
| 6,613,752 | B2 | 9/2003 | Kay et al. |
| 6,653,466 | B2 | 11/2003 | Matsuo |
| 6,740,793 | B2 | 5/2004 | Michaeli |
| 6,833,240 | B2 | 12/2004 | Engert et al. |
| 7,008,776 | B1 | 3/2006 | Jaye et al. |
| 7,306,794 | B2 | 12/2007 | Wilson et al. |
| 7,323,337 | B2 * | 1/2008 | Hanazono et al. ............ 435/456 |
| 7,416,849 | B2 | 8/2008 | Allen et al. |
| 7,510,867 | B2 | 3/2009 | Xiao |
| 7,795,493 | B2 * | 9/2010 | Phelps et al. ..................... 800/17 |
| 2002/0155446 | A1 | 10/2002 | Engert et al. |
| 2004/0203158 | A1 | 10/2004 | Hackett et al. |
| 2005/0003542 | A1 | 1/2005 | Kay et al. |
| 2005/0176665 | A1 | 8/2005 | McSwiggen |
| 2009/0241203 | A1 * | 9/2009 | Welsh et al. ..................... 800/3 |
| 2010/0146655 | A1 | 6/2010 | Fahrenkrug et al. |

FOREIGN PATENT DOCUMENTS

WO 2006036975 4/2006

OTHER PUBLICATIONS

Li et al. (2004) J. Reprod. Dev., vol. 50(2), 237-244.*
Dai et al., "Targeted disruption of the alpha 3-galactosyltranferase gene in cloned pigs" Nature Biotechnology, 2002, 251-255, vol. 20.
Mehta et al., "Deletion of LOX-1 reduces atherogensis in LDLR knocout mice fed high cholesteraol diet", Circulation Research, 2007, 1634-1642, vol. 100.
Willmann et al., Mammalian animal models for duchenne muscular dystrophy, Neuromuscular disorders, 2009, 241-249, vol. 19.
Yamanishi, Kiyofumi, "Gene-knockout mice with abnormal epidermal and hair follicular development" Journal of Dermatological Science 18, 1998, 75-89.
International Search Report and Written Opinion from Corresponding PCT Application No. PCT/US2011/024455 Dated Oct. 25, 2011, 10 pages.
Ahn et al., "The structural and functional diversity of dystrophin", Nature genetics, 3, 283-291 (1993).
Aiello et al., "Apolipoprotein B and a second major gene locus contribute to phenotypic variation of spontaneous hypercholesterolemia in pigs", Arterioscler Thromb Vasc Biol 14:409-419. (1994).
Banks et al.,"Neuromuscular synapses mediate motor axon branching and motoneuron survival during the embryonic period of programmed cell death," Developmental biology, 257, 71-84 (2003).
Banks et al., "Functional capacity of dystrophins carrying deletions in the N-terminal actin-binding domain," Hum Mol Genet, 16(17), 2105-2113 (2007).
Bar et al., "A novel product of the Duchenne muscular dystrophy gene which greatly differs from the known isoforms in its structure and tissue distribution", The Biochemical journal, 272, 557-560 (1990).
Barnea et al., "Specificity of expression of the muscle and brain dystrophin gene promoters in muscle and brain cells", Neuron, 5, 881-888 (1990).
Beggs et al., "Exploring the molecular basis for variability among patients with Becker muscular dystrophy: dystrophin gene and protein studies," Am J Hum Genet, 49, 54-67 (1991).
Bell et al., "Histopathological changes in Duchenne muscular dystrophy," J Neurol Sci, 7, 529-544 (1968).
Bernstein, "Exercise assessment of transgenic models of human cardiovascular disease", Physiol Genomics 13 (3):217-226 (2003).
Boyce et al., "Dystrophin is transcribed in brain from a distant upstream promoter," Proc Natl Acad Sci U S A, 88:1276-1280 (1991).
Branda et al.,"Talking about a Revolution: The Impact of Site-Specific Recombinases on Genetic Analysis in Mice," Dev. Cell, 6, 7-28 (2004).

(Continued)

Primary Examiner — Anne Marie S Wehbe
(74) Attorney, Agent, or Firm — Dardi & Herbert, PLLC.; Curtis B. Herbert

(57) ABSTRACT

Swine animal models comprising a genomic disruption of an endogenous gene chosen from the group consisting of a Low-Density Lipoprotein Receptor gene LDLR, Duchene's Muscular Dystrophy (DMD) gene, and hairless gene (HR). Methods of preparing transfected cells useful for making a transgenic animal comprising exposing a first group of cells to a transfection agent and reseeding the group with additional cells that have not been exposed to the agent. The transgenic animals are useful for medical and scientific animal models of human diseases and conditions, as well as sources for cells, tissues, and biomaterials.

7 Claims, 13 Drawing Sheets

(56) References Cited

OTHER PUBLICATIONS

Brown et al., "How LDL Receptors Influence Cholesterol and Atherosclerosis," Scientific American 251: 58-66 (1984).
Byers et al., "An alternative dystrophin transcript specific to peripheral nerve," Nature genetics, 4, 77-81 (1993).
Campbell, "Three muscular dystrophies: loss of cytoskeleton-extracellular matrix linkage", Cell, 80, 675-679 (1995).
Chamberlain et al., Dystrophin-deficient mdx mice display a reduced life span and are susceptible to spontaneous rhabdomyosarcoma. FASEB J, 21, 2195-2204 (2007).
Charreau et al., "Transgenesis in rats: technical aspects and models", Transgenic Res 5, 223-234 (1996).
Chelly et al., "Effect of dystrophin gene deletions on mRNA levels and processing in Duchenne and Becker muscular dystrophies," Cell, 63, 1239-1248 (1990).
Chetboul et al., "Tissue Doppler assessment of diastolic and systolic alterations of radial and longitudinal left ventricular motions in Golden Retrievers during the preclinical phase of cardiomyopathy associated with muscular dystrophy," American journal of veterinary research, 65, 1335-1341(2004).
Chetboul et al., "Tissue Doppler imaging detects early asymptomatic myocardial abnormalities in a dog model of Duchenne's cardiomyopathy," European heart journal, 25, 1934-1939 (2004).
Childers et al., "Eccentric contraction injury in dystrophic canine muscle," Archives of physical medicine and rehabilitation, 83, 1572-1578 (2002).
Cibelli et al.,"Cloned Transgenic Calves Produced from Nonquiescent Fetal Fibroblasts," Science 280, 1256-1258 (1998).
Cogoni et al.,"Transgene silencing of the al-1gene in vegetative cells of Neurospora is mediated by a cytoplasmic effector and does not depend on DNA-DNA interactions of DNA methylation," EMBO J., 15(12), 3153-3163 (1996).
Cogoni et al.,"Gene silencing in Neurospora crassa requires a protein homologous to RNA-dependent RNA polymerase," Nature, 399, 166-169 (1999).
Coleman, "Of mouse and man—what is the value of the mouse in predicting gene expression in humans?," Drug Discov Today 8(6); 233-235 (2003).
Cooper et al., "Mosaic expression of dystrophin in carriers of canine X-linked muscular dystrophy," Laboratory investigation; a journal of technical methods and pathology, 62(2), 171-178 (1990).
Cooper et al., "The homologue of the Duchenne locus is defective in X-linked muscular dystrophy of dogs," Nature, 334, 154-156 (1988).
Cox et al., "Dp71 can restore the dystrophin-associated glycoprotein complex in muscle but fails to prevent dystrophy," Nature genetics, 8, 333-339 (1994).
Daugherty, "Mouse models of atherosclerosis", Am J Med Sci; 323(1):3-10 (2002).
Deconinck et al., "Utrophin-dystrophin-deficient mice as a model for Duchenne muscular dystrophy," Cell, 90, 717-727 (1997).
D'Souza et al., "A novel dystrophin isoform is required for normal retinal electrophysiology." Hum Mol Genet, 4, 837-842 (1995).
Dupuy et al.,"Mammalian germ-line transgenesis by transposition," Proc Natl Acad Sci USA 99, 4495-4499 (2002).
Ervasti et al, "Deficiency of a glycoprotein component of the dystrophin complex in dystrophic muscle", Nature, 345, 315-319 (1990).
Fattori et al., "Drug-eluting stents in vascular intervention", Lancet 2003;361:247-249.
Fire et al.,"Potent and specific genetic interference by double-stranded RNA in Caenorhabditis elegans," Nature, 391, 806-811 (1998).
Glass et al., "Atherosclerosis. the road ahead", Cell, 104,503-516 (2001).
Gorecki et al., "Expression of four alternative dystrophin transcripts in brain regions regulated by different promoters," Hum Mol Genet, 1(7), 505-510 (1992).
Grady et al., "Skeletal and cardiac myopathies in mice lacking utrophin and dystrophin: a model for Duchenne muscular dystrophy," Cell, 90, 729-738 (1997).
Grainger et al., "Apolipoprotein E modulates clearance of apoptotic bodies in vitro and in vivo, resulting in a systemic proinflammatory state in apolipoprotein E-deficient mice," J Immunol;173:6366-6375 (2004).
Greenberg et al., "Reduced levels of dystrophin associated proteins in the brains of mice deficient for Dp71," Hum Mol Genet, 5(9), 1299-1303 (1996).
Greenberg et al., "Exogenous Dp71 restores the levels of dystrophin associated proteins but does not alleviate muscle damage in mdx mice," Nature genetics, 8, 340-344 (1994).
Grisham, "Interspecies comparison of liver carcinogenesis: implications for cancer risk assessment", Carcinogenesis 18(1):59-81 (1996).
Grunwald et al., "Identification of a novel Arg--> Cys mutation in the LDL receptor that contributes to spontaneous hypercholesterolemia in pigs", J Lipid Res; 40, 475-485 (1999).
Guatelli et al., "Isothermal, in vitro amplification of nucleic acids by a multienzyme reaction modeled after retroviral replication," Proc. Natl. Sci. USA, 87, 1874-1878 (1990).
Hasler-Rapacz et al., "Identification of a mutation in the low density lipoprotein receptor gene associated with recessive familial hypercholesterolemia in swine", Am J Med Genet, 76:379-386 (1998).
Henwood et al., "Lovastatin. A preliminary review of its pharmacodynamic properties and therapeutic use in hyperlipidaemia," Drugs; 36:429-454 (1988).
Ozawa et al., "Dystrophin-associated proteins in muscular dystrophy," Hum Mol Genet, 4, 1711-1716 (1995).
Partridge, "Models of dystrophinopathy, pathological mechanisms and assessment of therapies," Cambridge University Press, Cambridge, 310-331 (1997).
Pavlopoulos et al., "The DNA transposon Minos as a tool for transgenesis and functional genomic analysis in vertebrates and invertebrates," Genome biology 8 (suppl 1) article S2, S2.1-S2.7 (2007).
Piedrahita, "Targeted modification of the domestic animal genome," Theriogenology; 53, 105-116 (2000).
Prescott et al., "Development of Complex Atherosclerotic Lesions in Pigs with Inherited Hyper-LDL Cholesterolemia Bearing Mutant Alleles for Apolipoprotein B," Am J Pathol;139(1):139-147 (1991).
Prior et al., "A missense mutation in the dystrophin gene in a Duchenne muscular dystrophy patient," Nature Genetics, 4, 357-360 (1993).
Rapacz et al., "Lipoprotein mutations in pigs are associated with elevated plasma cholesterol and atherosclerosis," Science; 234(4783):1573-1577 (1986).
Rapaport et al., "Characterization and cell type distribution of a novel, major transcript of the Duchenne muscular dystrophy gene," Differentiation;, 49, 187-193 (1992).
Romano et al., "Quelling: transient inactivation of gene expression in Neurospora crassa by transformation with homologous sequences," Mol. Microbiol., 6(22), 3343-3353 (1992).
Ruof et al., "Lipid-Lowering Medication for Secondary Prevention of Coronary Heart Disease in a German Outpatient Population: The Gap Between Treatment Guidelines and Real Life Treatment Patterns," Prev Med; 35, 48-53 (2002).
Rybakova et al., "Dystrophin and Utrophin Bind Actin Through Distinct Modes of Contact," The Journal of Biological Chemistry, 281(15), 9996-10001(2006).
Schatzberg et al., "Alternative Dystrophin Gene Transcripts in Golden Retriever Muscular Dystrophy," Muscle & Nerve, 21, 991-998 (1998).
Schatzberg et al., "Molecular analysis of a spontaneous dystrophin 'knockout' dog," Neuromuscul Disord, 9, 289-295 (1999).
Serruys et al., "A Comparison of Balloon-Expandable-Stent Implantation with Balloon Angioplasty in Patients with Coronary Artery Disease," N Engl J Med; 331(8):489-495 (1994).
Serruys et al., "Periprocedural quantitative coronary angiography after Palmaz-Schatz stent implantation predicts the restenosis rate at six months. Results of a meta-analysis of the Belgian Netherlands Stent study (BENESTENT) I, BENESTENT II Pilot, BENESTENT II and MUSIC trials," J Am Coll Cardiol; 34(4):1067-1074. (1999).

Shimatsu et al., "Canine X-linked muscular dystrophy in Japan (CXMDJ)" Experimental animals / Japanese Association for Laboratory Animal Science, 52(2), 93-97 (2003).

Slater, "Structural determinants of the reliability of synaptic transmission at the vertebrate neuromuscular junction," J Neurocytol, 32, 505-522 (2003).

Summerton et al.,"Morpholino Antisense Oligomers: Design, Preparation, and Properties," Antisense Nucleic Acid Drug Dev. 7, 187-195 (1997).

Suzuki et al., "Glycoprotein-binding site of dystrophin is confined to the cysteine-rich domain and the first half of the carboxy-terminal domain", FEBS Letters, 308(2), 154-160 (1992).

Takeshima et al., "Amino-terminal deletion of 53% of dystrophin results in an intermediate Duchenne-Becker muscular dystrophy phenotype," Neurology, 44, 1648-1651(1994).

Thompson et al., "Germ Line Transmission and Expression of a Corrected HPRT Gene Produced by Gene Targeting in Embryonic Stem Cells," Cell, 56, 313-321 (1989).

Thompson, "Hairless is a nuclear receptor corepressor essential for skin function," Nucl Recept Signal, 7, 1-11 (2009).

Topol et al., "Outcomes at 1 year and economic implications of platelet glycoprotein IIb/IIIa blockade in patients undergoing coronary stenting: results from a multicentre randomised trial", Lancet; 354, 2019-2024 (1999).

Valentine et al., "Canine X-linked muscular dystrophy: selective involvement of muscles in neonatal dogs," Neuromuscul Disord, 1(1), 31-38 (1991).

Valentine et al., "Canine X-linked muscular dystrophy. An animal model of Duchenne muscular dystrophy: clinical studies," J Neurol Sci, 88, 69-81(1988).

Valentine et al., "Canine X-linked muscular dystrophy as an animal model of Duchenne muscular dystrophy: a review," American Journal of Medical Genetics, 42, 352-356 (1992).

Van Der Putten et al., "Efficient insertion of genes into the mouse germ line via retroviral vectors," Proc. Natl. Acad. Sci. USA, 82, 6148-6152 (1985).

Veniant et al., "Lipoprotein size and atherosclerosis susceptibility in Apoe(-/-) and Ldlr(-/-) mice," Arterioscler Thromb Vasc Biol; 21(10):1567-1570 (2001).

Vom Dahl et al., "Rotational atherectomy does not reduce recurrent in-stent restenosis: results of the angioplasty versus rotational atherectomy for treatment of diffuse in-stent restenosis trial (ARTIST)", Circulation J Am Heart Assoc; 105(5):583-588 (2002).

Wakayama et al., "Full-term development of mice from enucleated oocytes injected with cumulus cell nuclei," Nature, 394, 369-374 (1998).

Warner et al., "Expression of Dp260 in muscle tethers the actin cytoskeleton to the dystrophin-glycoprotein complex and partially prevents dystrophy," Hum Mol Genet, 11(9), 1095-1105 (2002).

Weiss, "Hot Prospect for New Gene Amplifier," Science, 254, 1292-1293 (1991).

Wheeler et al., "Transgenic technology and applications in swine," Theriogenology; 56,1345-1369 (2001).

Wilmut et al., "Viable offspring derived from fetal and adult mammalian cells," Nature, 385, 810-813 (1997).

Winnard et al., "Frameshift deletions of exons 3-7 and revertant fibers in Duchenne muscular dystrophy: mechanisms of dystrophin production," Am J Hum Genet, 56, 158-166 (1995).

Xu et al., "CMV-β-Actin Promoter Directs Higher Expression from an Adeno-Associated Viral Vector in the Liver than the Cytomegalovirus or Elongation Factor 1α Promoter and Results in Therapeutic Levels of Human Factor X in Mice," Hum. Gene Ther., 12, 563-573 (2001).

Yoshida et al., "Glycoprotein complex anchoring dystrophin to sarcolemma," Journal of Biochemistry, 108, 748-752 (1990).

Hann et al., "Building 'validated' mouse models of human cancer", Curr Opin Cell Biol; 13:778-784 (2001).

Harris, "Towards an ovine model of cystic fibrosis," Hum Mol Genet; 6(13):2191-2193 (1997).

Koenig et al., "The complete sequence of dystrophin predicts a rod-shaped cytoskeletal protein," Cell, 53, 219-228 (1988).

Hirata et al., "Efficient PRNP gene targeting in bovine fibroblasts by adeno-associated virus vectors," Cloning and Stem Cells; 6(1):31-36 (2004).

Hirata et al., "Targeted transgene insertion into human chromosomes by adeno-associated virus vectors," Nature Biotechnology, 20:735-738 (2002).

Holmes Jr. et al., "Results of Prevention of REStenosis with Tranilast and its Outcomes (PRESTO) trial," Circulation, J Am Heart Assoc;106:1243-1250 (2002).

Malik et al., "Acute platelet inhibition with abciximab does not reduce in-stent restenosis.", Circulation, J Am Heart Assoc;, 102:e110 (2000) (Abstract Only).

Janus et al., "Transgenic mouse models of Alzheimer's disease," Physiol Behav; 73, 873-886 (2001).

Jung et al., "Identification and characterization of the dystrophin anchoring site on β-dystroglycan," The Journal of Biological Chemistry, 270(45), 27305-27310 (1995).

Kawakami, "Tol2: a versitile gene transfer vector in vertebrates," Genome Biology, 8(suppl 1) article s7, S7.1-S7.10 (2007).

Kennerdell et al.,"Use of dsRNA-Mediated Genetic Interference to Demonstrate that frizzled and frizzled 2 Act in the Wingless Pathway," Cell, 95, 1017-1026 (1988).

Kiwaki et al., "Correction of Ornithine Transcarbamylase Deficiency in Adult spfash Mice and in OTC-Deficient Human Hepatocytes with Recombinant Adenoviruses Bearing the CAG Promoter," Human Gene Therapy, 7, 821-830 (1996).

Kohila et al., "Evaluation of the effects of aluminium, ethanol and their combination on rat brain synaptosomal integral proteins in vitro and after 90-day oral exposure," Arch Toxicol, 78, 276-282 (2004).

Kolber-Simonds et al., "Production of α-1,3-galactosyltransferase null pigs by means of nuclear transfer with fibroblasts bearing loss of heterozygosity mutations," Proc Natl Acad Sci U S A;101(19): 7335-7340 (2004).

Kuivenhoven et al., "The role of a common variant of the cholesteryl ester transfer protein gene in the progression of coronary atherosclerosis," N Engl J Med; 338(2):86-93 (1998).

Kuroiwa et al., "Sequential targeting of the genes encoding immunoglobulin-µ and prion protein in cattle," Nat Genet; 36(7):775-780 (2004).

Lafont, "The Cypher stent: no longer efficacious at three months in the porcine model?", Cardiovasc Res; 63, 575-576 (2004).

Lavitrano et al., "Efficient Production by sperm-mediated gene transfer of human decay accelerating factor (hDAF) transgenic pigs for xenotransplantation," Proc. Natl Acad. Sci. Acad. USA, 99(22), 14230-14235 (2002).

Lavitrano et al., "Sperm-mediated gene transfer," Reprod. Fert. Develop. 18, 19-23 (2006).

Law et al., "Dystrophin deficiency is associated with myotendinous junction defects in prenecrotic and fully regenerated skeletal muscle," Am J Pathol, 142(5), 1513-1523 (1993).

Le et al., "Monoclonal antibodies against the muscle-specific N-terminus of dystrophin: characterization of dystrophin in a muscular dystrophy patient with a frameshift deletion of exons 3-7," Am J Hum Genet, 53, 131-139 (1993).

Leaver, "A family of Tc1-like transposons from the genomes of fishes and frogs: evidence for horizontal transmission," Gene, 271, 203-214 (2001).

Lederfein et al., "A 71-kilodalton protein is a major product of the Duchenne muscular dystrophy gene in brain and other nonmuscle tissues", Proc Natl Acad Sci U S A, 89, 5346-5350 (1992).

Lee et al., "Concentrations and compositions of plasma lipoprotein subfractions of Lpb5-Lpu1 homozygous and heterozygous swine with hypercholesterolemia", J Lipid Res; 31, 839-847 (1990).

Leibovitz et al., "Exogenous Dp71 is a dominant negative competitor of dystrophin in skeletal muscle," Neuromuscul Disord, 12, 836-844 (2002).

Lidov et al., "Dp140: a novel 140 kDa CNS transcript from the dystrophin locus," Hum Mol Genet, 4(3), 329-335 (1995).

Lo, "Animal models of human disease. Transgenic and knockout models of autoimmunity: Building a better disease?", Clin Immunol Immunopathol; 79(2):96-104 (1996).

Lo, "Transformation by Iontophoretic Microinjection of DNA: Multiple Integrations Without Tandem Insertions," Mol. Cell. Biol., 3(10), 1803-1814 (1983).

Lowe et al., "Defective receptor binding of low density lipoprotein from pigs possessing mutant apolipoprotein B alleles," J Biol Chem; 263(30):15467-15473 (1988).

Lyons et al., "Structure and function of the neuromuscular junction in young adult mdx mice," J Neurocytology, 20, 969-981(1991).

Mahley et al., "An electrophoretic method for the quantitative isolation of human and swine plasma lipoproteins," Biochemistry; 13(9):1964-1968 (1974).

Marx, "Building better mouse models for studying cancer," Science; 299, 1972-1975 (2003).

Marz et al., "Safety of low-density lipoprotein cholestrol reduction with atorvastatin versus simvastatin in a coronary heart disease population (the TARGET TANGIBLE trial)", Am J Cardiol; 84:7-13 (1999).

Matsumura et al., "Immunohistochemical analysis of dystrophin-associated proteins in Becker/Duchenne muscular dystrophy with huge in-frame deletions in the NH2-terminal and rod domains of dystrophin," The Journal of clinical investigation, 93, 99-105 (1994).

McFadden et al., "Late thrombosis in drug-eluting coronary stents after discontinuation of antiplatelet therapy", Lancet; 364,1519-1521 (2004).

McIntyre et al., "Design and cloning strategies for constructing shRNA expression vectors," BMC Biotecnology 6:1 8 pages (2006).

McPherson et al., "Cerivastatin versus branded pravastatin in the treatment of primary hypercholesterolemia in primary care practice in Canada: a one-year, open-label, randomized, comparative study of efficacy, safety, and cost-effectiveness", Clin Ther, 23(9):1492-1507 (2001).

Mehlop et al., "Allergen-induced bronchial hyperreactivity and eosinophilic inflammation occur in the absence of IgE in a mouse model of asthma", Proc Natl Acad Sci U S A; 94:1344-1349 (1997).

Miskey et al., "The Ancient mariner Sails Again: Transposition of the Human Hsmar1 Element by a Reconstructed Transposase and Activities of the SETMAR Protein on Transposon Ends," Mol Cell Biol. 27(12), 4589-4600 (2007).

Miskey et al., "The Frog Prince: a reconstructed transposon from Rana pipiens with high tanspositional activity in vertebrate cells," Nucleic Acids Res. 31(23), 6873-6881 (2003).

Misquitta et al., "Targeted disruption of gene function in *Drosophila* by RNA interference (RNA-i): A role for nautilusin embryonic somatic muscle formation," Proc. Natl. Acad. Sci. USA, 96, 1451-1456 (1999).

Moer et al., "Stenting in small coronary arteries (SISCA) trial. A randomized comparison between balloon angioplasty and the heparin-coated beStent," J Am Coll Cardiol; 38(6):1598-1603 (2001).

Muni et al., "Problems with drug-eluting coronary stents—the FDA perspective," N Engl J Med; 351(16):1593-1595 (2004).

Muntoni et al., "Deletions in the 5' region of dystrophin and resulting phenotypes," Journal of Medical Genetics, 31, 843-847 (1994).

Nguyen et al., "Muscle Lesions Associated with Dystrophin Deficiency in Neonatal Golden Retriever Puppies," Journal of Comparative Pathology, 126, 100-108 (2002).

Novakovic et al., "Proximal Dystrophin Gene Deletions and protein Alterations in Becker Muscular Dystrophy," Annals of the New York Academy of Sciences, 1048, 406-410 (2005).

Nudel et al., "Duchenne muscular dystrophy gene product is not identical in muscle and brain," Nature, 337, 76-78 (1989).

Orban et al., "Tissue- and site-specific DNA recombination in transgenic mice," Proc. Natl. Acad. Sci. USA, 89, 6861-6865 (1992).

* cited by examiner

A

B

C

LDLR Partial CDS from MARC library est sequenced taccggtccggaattcccgggatatcgtcgacccacgcgtccgcccacacccacctgtggccccgccagcttccagtgcaacagctccacctgcatccc
tgagctgtgggcctgtgatggtgatcctgactgcgaggacggctcagacgagtggccacagcactgcaggagccacagctcatcactccccgagagg
agcaacaaccccctgctcagccctcgagttccactgccacagtggcgagtgcatccactccagctggcgctgcgacggagacactgactgcaaggaca
agtctgacgaggagaactgcgatgtggccacgtgccggcctgacgagttccagtgctcagacgggacctgcatccatggtagccggcagtgcgacag
ggaatatgactgcaaggacctgagcgacgagcagggctgtgtcaatgtgactctgtgcgaggggcccaacaagttcaagtgtcaaagcggcgagtg
catctccttggacaaagtgtgcaactcagtcagggactgccgggactggtcagacgagcccctcaaggagtgtgggaccaacgagtgtctggacaac
aagggtggctgctcccatatctgcaatgacctcaaagatcggctatgagtgcctctgtcccgagggcttccagctggtggataagcacagatgcgaa
gatatcgacgagtgtcaggacccagacgcctgcagccagatctgcgtgaacctcgagggcagctacaagtgccagtgtgaggagggcttccagctgg
agcctctcaccaaggcctgcaaggccataggccaccatcgcctacctcttcttcaccaaccgccacgaggtgaggaagatgaccctggaccgtagtgag
tacaccagcctcatccccaacctgaagaacgtggtcgctctggacactgaggtggccagcaacagaatctactggtctgatctgtctcagaggaagat
ctacagtaccccagatcaacagggcccccagcttttcctcctatgacaccattattggcgaagatctccaggccccccgatgggctggcggtggactggat
ccacagcaacatatactggactgactccatcctgggcactgtctccgtggctgacaccaagggcgtgaagaggaagactctcttccaagagaaaggc
tccaagccacgggccattgtggtggaccctgtccatggcttcatgtactggactgattggggaaccccgccaagatcaagaagggcggcctgaacgg
agtggacgtctactcgctggtgacggaggacatccagtggcccaatggcatcaccaagaatgtttctggcggccgctctagagtatccctcgagggc
cc

SEQ ID NO:1

FIG. 10

LDLR HinDIII Subclone sequence (includes exons 2-5)
agcttatgcctttgcagcctcaattttccttcgtactgttttcaattcagttttgtaatataccaaataattttctttactttgttttattttgttttgttttggc
tgccctgagatgtatggagttcctgggccagggatcagatctaagccacagttttgacctacctcagctgcagcaacaccagattcttaacccattctgc
tgggctggggattgaacctgtgtgccagtactaccaagacgcctccaattccattgtgccacagtgggaactcctcttttctttgttaacatgcaccaaa
gttctaatattttgttcccatagctcaatggatccatactttttttcaatattttattttatttttttcttttgattgcctcacctacggcctatggaaggaagt
tcttgagtttggggtggaatcagagctgcagctgccagcctacatcacagccatggcagcaccgaatccgagctgcatctgtgaactatgtcacagctt
gtggccatgctggatcttaagccactgagggaggccagggatcaaacccacatcctcacagaaacaacatttggtccttaacccactgagtcacaag
ggaactctctggatccatactctagactcagcatccaaccatgatgtcaaaatctcacattgttgacaaatctcttttgggtatactctttgcatcctccat
gaggtagatctatctcattgatgatatatataaaatatatgatatgtatatatttatataaaaattatatatttatgtataatttttttccatgatatgtgt
gtgtgtgtataattttttccttctctttggtcatgcctgtggcatgtggaagatcctggggccagggatcaaacccgagccacagccgtaataatgcca
gctccttaacctgctacatcatcaaggaactcaatcctccacgatgttgttggttcttgaaattgaatttgttcatatttcatttcctgggaacctgactgtt
acgataggattgtatttctggctcatttctcagctggcaagaaatagacacagggagtatggtcacttgctgatcctggcactgatgcttcatttccttttc
cttctctctcagtggaagagaaatgtgggagaaacgagttccagtgccgagacgggaaatgcatctcctacaagtggatttgtgatgggaacaccga
gtgcaaggacgggtccgatgagtccctggagacgtgcagtgagtcccttgggttgtgacctttctgaccatggtgggtgatagactcggtgggaatca
gcttgtgtattgatgcattctgctgtgaattaggatgtgggcggagaaggtatttctggaactttccttttaatggccctcccgtttttttttttaatgagatga
aaataggatttttttttttttttttttttttggtattttttacctcatatggaggttcccaggctaggggtctaaccggagctgtagccagatctgagcttcgtct
gtgacctataccacagctcatggcaacgctggacccttaacccactgagcaaggccagggatcgaacctgggtcctcatggatgcttgttgggttcgtt
ttccactgagccacaactggaactcctagattcttttctagtatagttattacaagatattgaatatagtttcctgtgctatgcagtaggtccttgtcgtcta
tctatttaatatgtagtgtcgtgtatctgttaattccaaactcctaatttatccctatagcccttaccaactggtcacttaattttttttccaatttaatataatt
tttatttatttagtcttttttgccttttcttgagtgctcctgtggcatatggaggttcccaggctaggggtctaatcggagctgtagccactggcctacgcc
agagccacagcaaggcaggatctgagccgtgtctgtgacctacaccacaactcacagcaacaccagatcctaacccactgagcaaggccagggat
cgaacccgcaacctcatggttcctagtcagattcgttaaccattggagccacccatgggaactcctataattttttattttattaaataaaatgtaaagg
ggagctcgctactcacttttgggctgctcccacagcatgcagaagttccccaggccagcgatggaaccctagcccacagcagtgacaatgccagatcc
ttaaccattaggccaccagggaactccaaggttttttcctttgcaaagcccagactggcaaggcaggttggtcttcctatgagttaagggtcaatgctgt
tttctcccacagtgtctgtcacctgcaagatagggactttagctgtgggggccgtgtcaaccgctgcattcctgagtcttggaggtgtgacggtcagca
ggactgcgagaatggctcagatgaggaaggctgttgtaagtggggtccctcacctcatgggccatgggcctcagccacgtccaagtgacccgaccag
attctggtctgaggtcagaatttgttcctccagctgagagttccacaaagaaacaaggctgatagtttcagatgggaaggcatgtggcagctggctctt
tgattttattcattatttataatttcctttcagctatataaacttttttttttttttttttttttttggccgcatctatggcatgtggaaattcctgggccagg
gatcaaacctgtgccacagcagtgacaaccctggatcattaacccactgagccactggggaactcttgtatagacatgtctttcatgaagtgaggctct
ttaaaaaaacaaaaacctctggacaggttgtaataacctataatgggagagaatgtaaaaggaagagaaatatatatatttctctctctcttttttttat
ttggtcgcatccactgcatatcaagttcccaggccagggactgaattcaaggtgcagctgcaacccactgcacagcagtgacaactgccagatcctta
acctgctgaacgaccagggaactccctcttttcatgttcttttccattatagtttattacaagaaattgaatgtggatccctgtgcaaactcttaaatagt
gcttcccatgtgcccagcccaacctgggaactttacacacgttcctcacagtaacaccttgagacacgaacagacgtccgaggcattgagagggccgg
gagctgggtgggtatctgggtggggcagtggttccaaatccagggcccctgactactaccccaggtccactcactgggcttggcctgtcctgggctcag
tgtccccatctatgcagtgggctggtgtagggcctcccggtaacctggctgtgatcttctgtctatttctgaagccccaagacgtgctcccaagatga
gttccgctgccaggacggcaagtgcatcgccccaaagtttgtgtgactcggaccgggactgcctggacggctcggatgaagcatcctgccccacac
ccacctgtggccccgccagcttccagtgcaacagctccacctgcatccctgagctgtgggcctgtgatggtgatcctgactgcgaggacggctcagacg
agtggccacagcactgcaggagccacagctcatcactccccgagaggagcaacaaccccctgctcagccctcgagttccactgccacagtggcgagtg
catccactccagctggcgctgcgacggagacactgactgcaaggacaagtctgacgaggagaactgcggtaggggcgccttgggggatcccttcacct
gtccctgggccctcctgtgtgggggggtgggggctgccagtgcctttaggtggttctgatcttggagagacagctgtgagtgatggctcgaagcaaga
tcttaattctctgctcgggaatcaaacctgggcagcctgggtgttccgtggtgggctcagtggttaacgaatctgactaggaaccatgagggttgcagg

FIG. 11-1 ttcgatccctggccttgctcagtgggttaaggatctggtgttgctgtgagctgtggtgtaggttgcagacgcagctcagatctggtgttgctgtggctctg
gcataggccagcggctacagctccgattcaacccctagcctgggaacctccatatgccgtgagtgaggccctagaaaatacaaaaaacaaaacctga
gcagcctgggtgaaaaccaggaatcttagctagaggctggaagcagaattgccttgattcttgctccctgttgaaaagcaagaatgtttcaaggagac
aaagactgtaaaaacaggtacaaagtttattgtcagagacacagtgtgacatgttggagagcacacagggaagtagtttatttaggagttcccatcat
agctcagtggttaacgaacccacctagcatccatgaggacacaggttcgatccttggcctcgctcagtgggttaaggatccggcattgccgtgagctgt
ggtgtaggtcacaggctaggattggatctcgagtggctgtggctgtggtgtcggccagcagctacagtcccccagtttgaccccctagcctgggaacttc
cacatgctgtgcgtgtggccctaaaaagactgaaaaagaaaaagtagtttatttaagtcagagcaaagcagtaatccacacccaaaagaggagtg
ctggcgttcccccccgaatgaagagcgagccagagaggtgatttaaaccactttatagacgggtctactgggtctttgtttttctttgaccagttatcct
gttttatttctcacacctgaccagacccagggccctccctgatctgtgtgtgcagcttttggtcaagatggatttcagagcaaagtgttatgggagggcat
caggacctactatggcctggtaccccacctccgtttttgaccccaagagtttctctgtgtatatataactggggaggtcttcttgacccccaggagtaat
tgaagtagtcagcttatctctctatactagggagttcccatcgtggctcagtggtaaggaacctgactagtatccattaggacgcaggtttgaaccctgt
cctcactcagtaggttaaggatctggtgttgccgtgagttctgtaggttgcagactcagctgggacctggtgttgctgtggctgtgatctaggccggcag
cggcagcagcagcagtagctccgattcaacccctagcctgggaacttctatatgccgagggtgctgccctaaaaagaaaaaaaaaatcttttta
ttccagcagagctcaggtcctgccattaactttctccttgacatgtcaaaaagaagcaaagcccaaattaccaagcctgacgtgtcccagctgttctca
gcccaggggcccatctacttcctacctcagttcaatgatttcgcatcacacagcaagaaagttggccccattcaggtttcttccaatctttctgatcactt
ggaggacaagctccatctcaaatgtctccttaattagtctcttttgacaaggggcacacactgcaacccgcagtgtcttttttgtccagaaatcatcctgg
gctccgggcctggctggtgacgtccctgctgcgtgaccettggccaaggacttagcctcactgtgccgtgatcccctccctgttatggggcaacagcct
tggccttctcagaccttgggcagaatccagcgccaccgatagaactttctgtgaggctgccccgtgcaccagagctgggcagtgtggctggttcaccga
agcccagaattcttaggtttatttcgctttaactaattgaaagttaaatggccacgtgtagttagtggctcctgcataggagagagtgccagtcaaggac
ctggccctgaatggaggccgttcacccatgactaatgatgtaggaagtttccctcttctgtttctttggtacctttgcccttgggcacagtttcagagttg
cactcactgtatagttgccactatacagacttttgtttatttgttgttttagattaacaaatcagtatgttctttttaaaaaaagtttattatagttgattta
caatgttctgtcgatttagattttaaattttttttaatttattttattttttaatttttattttttattttttgcttttgagggccaccccctcggcat
atggaggttccaggctaggggtctagtccgagctgtagccgccagcctacgccacagccacagcaattcaggatccaagccgcgtctgtgacctac
accacagctcacagcaacactgatccctaacccactgagcaaggtcaggatcaaacccgcaacctcatggttcctagtcagattcgttaaccactg
agccacaatgggaactccaaatgttacttttttaagaacaattagagacttgtctgtgattggttctaaaactgaacacaaacttggttaatccccatgc
cttgagcaggcttccctcattcttacagatgaggaaaccaaggcacagaaaggcagagtagccttctgaggacacacacctatgaaaactatacttc
ccatatgtaccctactattttagctgtcgtctgagtgcatttttcattagagttaatgctcagttgtgttttttgttccttattgcaaagatgaacaaatggttt
aaaaatcatcatgggaattcccgctctggtgcagcgggttaagaatctgacagcaacagctctggtcgctgtggaggtgcaggttcgatctccagc
cctgtgctctggcttaaggatccagcattgctgcagctgtggcctaggttgcaactgtggcttgcattcgattcttggccctgggactttttttaatatgcc
acaagtgtggctattaaaaaaaaaaaaaaaagaatcattctgggagtttccttgtgcaggtacagggggttaaggatccagcatttcactgctatggc
cctggttactgctgtgtcatgagttcactccctggccccccagaatttctgtatgccatagacatggccccaaaacacaaaaacacaaaagggattcttt
tctatcctgtgagaaaccataatggaaataaaaaagaatatgtgtgttacagataaaaactgagtcacttttacagtacagcagaaattaacacaatgt
tgttaatcaactatacttccttaaaattaaaaaaacacgatcattctaaatgaaaggaagcaaaacaaagcaaaaacaggatcattctatgtaacag
aaattggcacaagattgttattcaacttttaataaaaaaagtttattataaattggctgcacccaagacatgcacctgaggcatgtggaagtttctgcac
catagctgtaactagagtgagagcagtgacaaggccagatccttacccactgagccacccagggaactcctgagggtctgccagcttttaataaattt
cctggttttttgtgtttattgtttgtgtcttttttgccatttcttgggcccgctccctatggcatatggaggtttcccaggctaggggtccaattggagctgtag
ccgccggcctaccccagaaccacagcaacgcgggatccgagccacgtctgcaacctacaccacagctcatgggcaatgctggatccttaacccactg
agcaaggccagggatcaaacccgcaacctcacgcttcctagttggattcgttaaccgctgagccacgacgggaactccatgaatttcctgttttgaaac
atgcatgtgaagacaaagcagagagaagtctaagaaaacttaatatttgtgtattgcccattttcttatcttccacacttggctctgcctctcccagatgt
ggccacgtgccggcctgacgagttccagtgctcagacgggacctgcatccatggtagccggcagtgcgacaggggaatatgactgcaaggacctgagc
gacgagcagggctgtgtcaatggtgagctctgttccatgggggtcctgggcctggggggagatgtggggaggagcctcctgggtcctcactggctgtttgt
ccttggggaaattagttgacctctctgagcctcacttctgcttatctgaaaactgtgcaaaatgaaagccctacctcaggactgtgagaatgaggtcag

FIG. 11-2 agtgtagagagctcatatacttaccctgagttacatgcagatataactccatgtaaaaagcactttgctgaatctacaacattgcagttcctgttcttgg
gaatgatgccaggagaaacttagacctgtgcactggaggatagaccctggaacaggcagagcagcactgtcctaacagcaaaacattagaagcaac
ccaaatgtttatcagcagtagaattaatttaattaatttattttttggcttaattttaaggccacatccacggcatatggaggttcccaggctaggggtct
aattggagctgtagcagccagccttcaccagagccacagaaacaacagatccgagctgcgtctgcaacctacaccacagcttgcagcaacgccggat
ccttaaaccactgagcgaggctagggttcaaacccatgccctcacgga

SEQ ID NO:2

SEQUENCE LISTING

<160> NUMBER OF SEQ ID NOS: 2

<210> SEQ ID NO 1
<211> LENGTH: 1368
<212> TYPE: DNA
<213> ORGANISM: Sus scrofa

<400> SEQUENCE: 1

```
taccggtccg gaattccgg  gatatcgtcg  acccacgcgt  ccgcccacac  ccacctgtgg      60
ccccgccagc ttccagtgca acagctccac  ctgcatccct  gagctgtggg  cctgtgatgg     120
tgatcctgac tgcgaggacg gctcagacga  gtggccacag  cactgcagga  gccacagctc     180
atcactcccc gagaggagca acaaccctg   ctcagccctc  gagttccact  gccacagtgg     240
cgagtgcatc cactccagct ggcgctgcga  cggagacact  gactgcaagg  acaagtctga     300
cgaggagaac tgcgatgtgg ccacgtgccg  gcctgacgag  ttccagtgct  cagacgggac     360
ctgcatccat ggtagccggc agtgcgacag  ggaatatgac  tgcaaggacc  tgagcgacga     420
gcagggctgt gtcaatgtga ctctgtgcga  ggggcccaac  aagttcaagt  gtcaaagcgg     480
cgagtgcatc tccttggaca aagtgtgcaa  ctcagtcagg  gactgccggg  actggtcaga     540
cgagcccctc aaggagtgtg ggaccaacga  gtgtctggac  aacaagggtg  gctgctccca     600
tatctgcaat gacctcaaag atcggctatg  agtgcctctg  tccccgaggg  cttccagctg     660
gtggataagc acagatgcga agatatcgac  gagtgtcagg  acccagacgc  ctgcagccag     720
atctgcgtga acctcgaggg cagctacaag  tgccagtgtg  aggagggctt  ccagctggag     780
```

```
cctctcacca aggcctgcaa ggccataggc accatcgcct acctcttctt caccaaccgc      840
cacgaggtga ggaagatgac cctggaccgt agtgagtaca ccagcctcat ccccaacctg      900
aagaacgtgg tcgctctgga cactgaggtg gccagcaaca gaatctactg gtctgatctg      960
tctcagagga agatctacag tacccagatc aacagggccc ccagcttttc ctcctatgac     1020
accattattg gcgaagatct ccaggccccc gatgggctgg cggtggactg gatccacagc     1080
aacatatact ggactgactc catcctgggc actgtctccg tggctgacac caagggcgtg     1140
aagaggaaga ctctcttcca agagaaaggc tccaagccac gggccattgt ggtggaccct     1200
gtccatggct tcatgtactg gactgattgg ggaaccccg ccaagatcaa gaagggcggc     1260
ctgaacggag tggacgtcta ctcgctggtg acggaggaca tccagtggcc caatggcatc     1320
accaagaatg tttctggcgg ccgctctaga gtatccctcg aggggccc                  1368

<210> SEQ ID NO 2
<211> LENGTH: 8654
<212> TYPE: DNA
<213> ORGANISM: Sus scrofa

<400> SEQUENCE: 2
agcttatgcc tttgcagcct caattttcct tcgtactgtt ttcaattcag ttttgtaata       60
taccaaataa ttttctttac tttgtttta ttttgttttg ttttggctg ccctgagatg       120 tatggagttc ctgggccagg atcagatct aagccacagt tttgacctac ctcagctgca      180
gcaacaccag attcttaacc cattctgctg ggctgggggat tgaacctgtg tgccagtact      240
accaagacgc ctccaattcc attgtgccac agtgggaact cctcttttct tgttaacat       300 gcaccaaagt tctaatattt tgttcccata gctcaatgga tccatacttt ttttcaata       360 ttttatttta tttttttctt ttgattgcct cacctacggc ctatggaagg aagttcttga      420
gtttggggtg gaatcagagc tgcagctgcc agcctcatc acagccatgg cagcaccgaa       480
tccgagctgc atctgtgaac tatgtcacag cttgtggcca tgctggatct ttaagccact      540
gagggaggcc agggatcaaa cccacatcct cacagaaaca catttggtc cttaacccac       600 tgagtcacaa gggaactctc tggatccata ctctagactc agcatccaac catgatgtca      660
aaatctcaca ttgttgacaa atctctttg ggtatactct ttgcatcctc catgaggtag       720
atctatctca ttgatgatat atataaaata tatatgatat gtatatattt ataaaaaat       780 tatatattta tgtataattt ttttccatga tatgtgtgtg tgtgtataat tttttccctt      840
tctctttggt catgcctgtg gcatgtgaa gatcctgggg ccaggatca aacccgagcc       900 acagccgtaa taatgccagc tccttaacct gctacatcat caaggaactc aatcctccac       960
gatgttgttg gttcttgaaa ttgaatttgt tcatatttca tttcctggga acctgactgt     1020
tacgatagga ttgtatttct ggctcatttc tcagctggca agaaatagac acagggagta     1080
tggtcacttg ctgatcctgg cactgatgct tcatttcctt ttccttctct ctcagtggaa     1140
gagaaatgtg ggagaaacga gttccagtgc cgagacggga aatgcatctc ctacaagtgg     1200
atttgtgatg ggaacaccga gtgcaaggac gggtccgatg agtccctgga cacgtgcagt     1260 gagtccccctt gggttgtgac ctttctgacc atggtgggtg atagactcgg tgggaatcag     1320
cttgtgtatt gatgcattct gctgtgaatt aggatgtggg cggagaaggt atttctggaa     1380 ctttcctttta atggccctcc cgttttttttt ttaatgagat gaaaatagga ttttttttt      1440 tttttttttt tttggtattt ttacctcata tggaggttcc caggctaggg gtctaaccgg     1500
agctgtagcc agatctgagc ttcgtctgtg acctatacca cagctcatgg caacgctgga     1560
```

```
cccttaaccc actgagcaag gccagggatc gaacctgggt cctcatggat gcttgttggg    1620
ttcgttttcc actgagccac aactggaact cctagattct tttctagtat agttattaca    1680
agatattgaa tatagtttcc tgtgctatgc agtaggtcct tgtcgtctat ctatttaata    1740
tgtagtgtcg tgtatctgtt aattccaaac tcctaattta tccctatagc ccttaccaac    1800
tggtcactta attttttcc aatttaatat aattttatt ttattttagt cttttgcct      1860 tttcttgagt gctcctgtgg catatggagg ttcccaggct aggggtctaa tcggagctgt    1920
agccactggc ctacgccaga gccacagcaa ggcaggatct gagccgtgtc tgtgacctac    1980
accacaactc acagcaacac cagatcctta acccactgag caaggccagg gatcgaaccc    2040
gcaacctcat ggttcctagt cagattcgtt aaccattgga gcccaccat gggaactcct    2100 ataattttta ttttattaaa taaaatgtaa aggggagctc gctactcact tttgggctgc    2160
tcccacagca tgcagaagtt ccccaggcca gcgatggaac cctagcccac agcagtgaca    2220
atgccagatc cttaaccatt aggccaccag ggaactccaa ggttttttcc tttgcaaagc    2280
ccagactggc aaggcaggtt ggtcttccta tgagttaagg gtcaatgctg ttttctccca    2340
cagtgtctgt cacctgcaag ataggggact ttagctgtgg gggccgtgtc aaccgctgca    2400
ttcctgagtc ttggaggtgt gacggtcagc aggactgcga gaatggctca gatgaggaag    2460
gctgttgtaa gtgggtccc tcacctcatg ggccatgggc ctcagccacg tccaagtgac    2520
ccgaccagat tctggtctga ggtcagaatt tgttcctcca gctgagagtt ccacaaagaa    2580
acaaggctga tagtttcaga tgggaaggca tgtggcagct ggctctttga ttttattcat    2640
tatttataat ttccttttca gctatataaa cttttttttt tttttttttt ttttttggc    2700 cgcatctatg gcatgtggaa attcctgggc cagggatcaa acctgtgcca cagcagtgac    2760
aaccctggat cattaaccca ctgagccact ggggaactct tgtatagaca tgtctttcat    2820
gaagtgaggc tctttaaaaa aacaaaaacc tctggacagg ttgtaataac ctataatggg    2880
agagaatgta aaaggaagag aaatatatat atttctctct ctcttttttt tatttggtcg    2940
catccactgc atatcaagtt cccaggccag ggactgaatt caaggtgcag ctgcaaccca    3000
ctgcacagca gtgacaactg ccagatcctt aacctgctga acgaccaggg aactccctct    3060
ttttcatgtt cttttccatt atagtttatt acaagaaatt gaatgtggat ccctgtgcaa    3120
actcttaaat agtgctccc atgtgcccag cccaacctgg gaactttaca cacgttcctc     3180
acagtaacac cttgagacac gaacagacgt ccgaggcatt gagagggccg ggagctgggt    3240
gggtatctgg gtggggcagt ggttccaaat ccagggcccc tgactactac cccaggtcca    3300
ctcactgggc ttggcctgtc ctgggctcag tgtccccatc tatgcagtgg gctggtgtag    3360
ggcctccccg gtaacctggc tgtgatcttc tgtctatttc tgaagccccc aagacgtgct    3420
cccaagatga gttccgctgc caggacggca agtgcatcgc cccaaagttt gtctgtgact    3480
cggaccggga ctgcctggac ggctcggatg aagcatcctg ccccacaccc acctgtggcc    3540
ccgccagctt ccagtgcaac agctccacct gcatccctga gctgtgggcc tgtgatggtg    3600
atcctgactg cgaggacggc tcagacgagt ggccacagca ctgcaggagc cacagctcat    3660
cactccccga gaggagcaac aaccctgct cagccctcga gttccactgc cacagtggcg    3720
agtgcatcca ctccagctgg cgctgcgacg gagacactga ctgcaaggac aagtctgacg    3780
aggagaactg cggtagggc gccttgggga tcccttcacc tgtccctggg ccctcctgtg    3840 tgggggtgg ggggctggcc agtgccttta ggtggttctg atcttggaga acagctgtg     3900 agtgatggct cgaagcaaga tcttaattct ctgctcggga atcaaacctg gcagcctgg    3960
```

-continued

```
gtgttccgtg gtgggctcag tggttaacga atctgactag gaaccatgag ggttgcaggt    4020
tcgatccctg gccttgctca gtgggttaag gatctggtgt tgctgtgagc tgtggtgtag    4080
gttgcagacg cagctcagat ctggtgttgc tgtggctctg gcataggcca gcggctacag    4140
ctccgattca accectagcc tgggaacctc catatgccgt gagtgaggcc ctagaaaata    4200 caaaaacaa aacctgagca gcctgggtga aaaccaggaa tcttagctag aggctggaag    4260
cagaattgcc ttgattcttg ctccctgttg aaaagcaaga atgtttcaag agacaaaga    4320 ctgtaaaaac aggtacaaag tttattgtca gagacacagt gtgacatgtt ggagagcaca    4380
cagggaagta gtttatttag gagttcccat catagctcag tggttaacga acccacctag    4440
catccatgag gacacaggtt cgatccttgg cctcgctcag tgggttaagg atccggcatt    4500
gccgtgagct gtggtgtagg tcacaggcta ggattggatc tcgagtggct gtggctgtgg    4560
tgtcggccag cagctacagt cccccagttt gaccectagc ctgggaactt ccacatgctg    4620
tgcgtgtggc cctaaaaaga ctgaaaaaag aaaagtagt ttatttaagt cagagcaaag    4680
cagtaatcca caccaaaag aggagtgctg gcgttccccc cccgaatgaa gagcgagcca    4740
gagaggtgat ttaaaccact ttatagacgg gtctactggg tctttgtttt tctttgacca    4800
gttatcctgt tttatttctc acacctgacc agacccaggg ccctcctga tctgtgtgtg    4860 cagcttttgg tcaagatgga tttcagagca aagtgttatg ggagggcatc aggacctact    4920
atggcctggt accccacctc cgttttgac ccccaagagt ttctctgtgt atatataact    4980
ggggaggtct tcttgacccc caggagtaat tgaagtagtc agcttatctc tctatactag    5040
ggagttccca tcgtggctca gtggtaagga acctgactag tatccattag gacgcaggtt    5100
tgaaccctgt cctcactcag taggttaagg atctggtgtt gccgtgagtt ctgtaggttg    5160
cagactcagc tgggacctgg tgttgctgtg gctgtgatct aggccggcag cggcagcagc    5220
agcagcagta gctccgattc aacccctagc ctgggaactt ctatatgccg agggtgctgc    5280
cctaaaaaga aaaaaaaaaa tcttttttatt ccagcagagc tcaggtcctg ccattaactt    5340
tctccttgac atgtcaaaaa gaagcaaagc ccaaattacc aagcctgacg tgtcccagct    5400
gttctcagcc caggggccca tctacttcct acctcagttc aatgatttcg catcacacag    5460
caagaaagtt ggccccattt caggtttctt ccaatctttc tgatcacttg gaggacaagc    5520
tccatctcaa atgtctcctt aattagtctc ttttgacaag gggcacacac tgcaacccgc    5580
agtgtctttt tgtccagaaa tcatcctggg ctccgggcct ggctggtgac gtccctgctg    5640 cgtgacccctt ggccaaggac ttagcctcac tgtgccgtga tcccctcccc tgttatgggg    5700
caacagcctt ggccttctca gaccttgggc agaatccagc gccaccgata gaactttctg    5760
tgaggctgcc ccgtgcacca gagctgggca gtgtggctgg ttcaccgaag cccagaattc    5820
ttaggtttat ttcgctttaa ctaattgaaa gttaaatggc cacgtgtagt tagtggctcc    5880
tgcataggag agagtgccag tcaaggacct ggccctgaat ggaggccgtt cacccatgac    5940
taatgatgta ggaagtttcc ctcttctgt ttctttggta cctttgccct tgggcacagt    6000
tttcagagtt gcactcactg tatagttgcc actatacaga ctttttgttt atttgttgtt    6060
tttagattaa caaatcagta tgttctttt aaaaaagtt tattatagtt gatttacaat    6120
gttctgtcga tttagatttt taaatttttt ttaatttatt tttatttatt ttattttatt    6180
ttttattttt tatttttttt gcttttgagg gccaccccct cggcatatgg aggttcccag    6240
gctagggggt ctagtccgag ctgtagccgc cagcctacgc cacagccaca gcaattcagg    6300
atccaagccg cgtctgtgac ctacaccaca gctcacagca acactggatc cctaacccac    6360
```

```
tgagcaaggt cagggatcaa acccgcaacc tcatggttcc tagtcagatt cgttaaccac    6420
tgagccacaa tgggaactcc aaatgttact ttttaagaac aattagagac tttgtctgtg    6480
attggttcta aaactgaaca caaacttggt taatccccat gccttgagca ggcttccctc    6540
attctttaca gatgaggaaa ccaaggcaca gaaaggcaga gtagccttct gaggacacac    6600
acctatgaaa actatacttc ccatatgtac cctactatttt agctgtcgt ctgagtgcat    6660 ttttcattag agttaatgct cagttgtgtt tttgttcctt attgcaaaga tgaacaaatg    6720
gtttaaaaat aaaatcatgg gaattcccgc tctggtgcag cgggttaaga atctgacagc    6780
aacagctctg gtcgctgtgg aggtgcaggt tcgatctcca gccctgtgct ctggcttaag    6840
gatccagcat tgctgcagct gtggcctagg ttgcaactgt ggcttgcatt cgattcttgg    6900
ccctgggact ttttttaata tgccacaagt gtggctatta aaaaaaaaaa aaaaagaat    6960 cattctggga gtttccttgt gcaggtacag gggttaagga tccagcattt cactgctatg    7020
gccctggtta ctgctgtgtc atgagttcac tccctggccc ccagaatttc tgtatgccat    7080
agacatggcc cccaaaacac aaaaacacaa aagggattct tttctatcct gtgagaaacc    7140
ataatggaaa taaaaagaa tatgtgtgtt acagataaaa actgagtcac tttacagtac    7200
agcagaaatt aacacaatgt tgttaatcaa ctatacttcc ttaaaattaa aaaaacacga    7260
tcattctaaa tgaaaggaag caaaacaaag caaaaacagg atcattctat gtaacagaaa    7320
ttggcacaag attgttattc aactttaata aaaaaagttt attataaatt ggctgcaccc    7380
aagacatgca cctgaggcat gtggaagttt ctgcaccata gctgtaacta gagtgagagc    7440
agtgacaagg ccagatcctt acccactgag ccacccaggg aactcctgag ggtctgccag    7500 cttttttaata aatttcctgg tttttttgtgt tttattgttt gtgtcttttt gccatttctt    7560
gggcccgctc cctatggcat atggaggttc ccaggctagg ggtccaattg gagctgtagc    7620
cgccggccta ccccagaacc acagcaacgc gggatccgag ccacgtctgc aacctacacc    7680
acagctcatg ggcaatgctg gatccttaac ccactgagca aggccaggga tcaaacccgc    7740
aacctcacgc ttcctagttg gattcgttaa ccgctgagcc acgacgggaa ctccatgaat    7800
ttcctgtttt gaaacatgca tgtgaagaca aagcagagag aagtctaaga aaacttaata    7860
tttgtgtatt gcccatttc ttatcttcca cacttggctc tgcctctccc agatgtggcc    7920
acgtgccggc ctgacgagtt ccagtgctca gacgggacct gcatccatgg tagccggcag    7980
tgcgacaggg aatatgactg caaggacctg agcgacgagc agggctgtgt caatggtgag    8040
ctctgttcca tgggggtcctg ggcctggggg agatgtgggg aggagcctcc tgggtcctca    8100
ctggctgttt gtccttgggg aaattagttg acctctctga gcctcacttc tgcttatctg    8160
aaaactgtgc aaaatgaaag ccctacctca ggactgtgag aatgaggtca gagtgtagag    8220
agctcatata cttaccctga gttacatgca gatataactc catgtaaaaa gcactttgct    8280
gaatctacaa cattgcagtt cctgttcttg gaatgatgc caggagaaac ttagacctgt    8340
gcactggagg atagaccctg aacaggcag agcagcactg tcctaacagc aaaacattag    8400
aagcaaccca aatgtttatc agcagtagaa ttaatttaat taatttattt ttttggctta    8460
attttaaggc cacatccacg gcatatggag gttcccaggc tagggtcta attggagctg    8520 tagcagccag ccttcaccag agccacagaa acaacagatc cgagctgcgt ctgcaaccta    8580
caccacagct tgcagcaacg ccggatcctt aaaccactga gcgaggctag ggttcaaacc    8640
catgccctca cgga    8654
```

METHODS AND MATERIALS FOR PRODUCING TRANSGENIC ARTIODACTYLS

CROSS REFERENCE TO RELATED APPLICATIONS

This application is a continuation of pending U.S. patent application Ser. No. 13/025,373 filed on Feb. 11, 2011 which claims priority to U.S. Provisional Application Nos. 61/303,523 filed Feb. 11, 2010 and 61/309,949 filed Mar. 3, 2010 which are hereby incorporated by reference herein.

FIELD OF THE INVENTION

The field of the invention relates to the production of transgenic artiodactyls, for instance pigs. Some aspects of the field relate to the genes manipulated to make the transgenic animal, for instance the low density lipoprotein receptor (LDLR) gene, Duchene's Muscular Dystrophy (DMD) gene, and the Hairless (HR) gene. Other aspects of the field relate to techniques for transforming swine cells.

BACKGROUND

Swine are an important agricultural commodity and biomedical model. Manipulation of the pig genome provides opportunity to improve production efficiency, enhance disease resistance, and add value to swine products. Genetic engineering can also expand the utility of pigs for modeling human disease, developing clinical treatment methodologies, or donating tissues for xenotransplantation. Heightened interest in such models for human disease and in the production of transgenic livestock for biomedical applications have increased the need for improved methods for transgenesis, as well as for particular models of various diseases.

SUMMARY OF THE INVENTION

Herein is described a method for making a stably transfected swine cell. The arts of transgenic artiodactyl cloning have generally lacked a consistent and robust technique for making stably transfected swine cells. Once a stably transfected cell is produced, transgenic swine may be made and then used to meet a growing need for uniform animal models of human pathologies.

One aspect of the method is that a first group of cells may be treated to introduce an exogenous gene and then mixed with a second group of cells that have not been treated. A series of collection and selection processes may be overlaid with this step being repeated. This method is exemplified herein in the context of the production of swine cells with a knockout for the low density lipoprotein receptor (LDLR), Dystrophin gene (DMD), and Hairless gene (HR) in male and female domestic and miniature swine cells.

Transgenic animals with knockouts for LDLR, and DMD gene are described herein. These animals are useful for modeling atherosclerosis and Duchenne's muscular dystrophy, respectively. Knockouts for HR are useful for providing components for medical devices, including dermal derived biomaterials and for the use of pigs as models for transdermal drug delivery, and other applications benefiting from denuded skin.

An embodiment of the invention is a transgenic swine comprising a genomic disruption of an endogenous gene chosen from the group consisting of a Low-Density Lipoprotein Receptor gene (LDLR), Duchene's Muscular Dystrophy (DMD) gene, and hairless gene (HR). Said genomic disruption may be engineered for preventing expression of a functional protein and/or preventing expression on any protein. The swine may be homozygous or heterozygous for said disrupted gene. The swine may be free of a marker gene. The swine may exhibit a phenotype chosen from the group consisting of hypercholesterolemia, atherosclerosis, and atherosclerotic lesions. Some of all of the cells in the animal may be disrupted with respect to the DMD, LDLR or HR gene. The disruption may be inducible upon administration of an induction agent. The swine may be chosen from the group consisting of pig, miniature pig, and Ossabaw pig. Tissue recovered from such a pig is included, as well as methods of recovering said tissue.

An embodiment is a transfected somatic swine cell comprising a disrupted gene chosen from the group consisting of a Low-Density Lipoprotein Receptor gene (LDLR), Duchene's Muscular Dystrophy (DMD) gene, and a hairless gene (HR). The cell may be chosen from the group consisting of embryonic blastomere, fetal fibroblast, adult ear fibroblast, and granulosa cell. A transgenic swine may be prepared by nuclear transfer of such a cell.

An embodiment is a method of introducing an exogenous nucleic acid into a swine cell in vitro comprising exposing a first group of swine cells to a transfection agent that comprises an exogenous nucleic acid during a first culture time period and subsequently adding a second group of swine cells to the first group for a second culture time period, wherein the second group of cells have not been exposed to the transfection agent. The first group of cells may be chosen from the group consisting of primary fetal swine cells and swine fibroblasts. A ratio of the second group of cells to the first group of cells may be between 1:1 and 20:1. The exogenous nucleic acid may disrupts a target gene chosen from the group consisting of a Low-Density Lipoprotein Receptor gene (LDLR), Duchene's Muscular Dystrophy (DMD) gene, and a hairless gene (HR).

Figure 4:
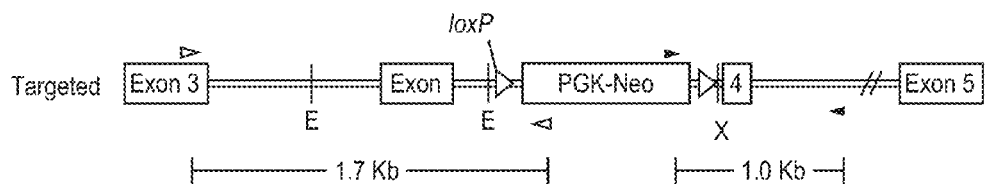
Figure 4:
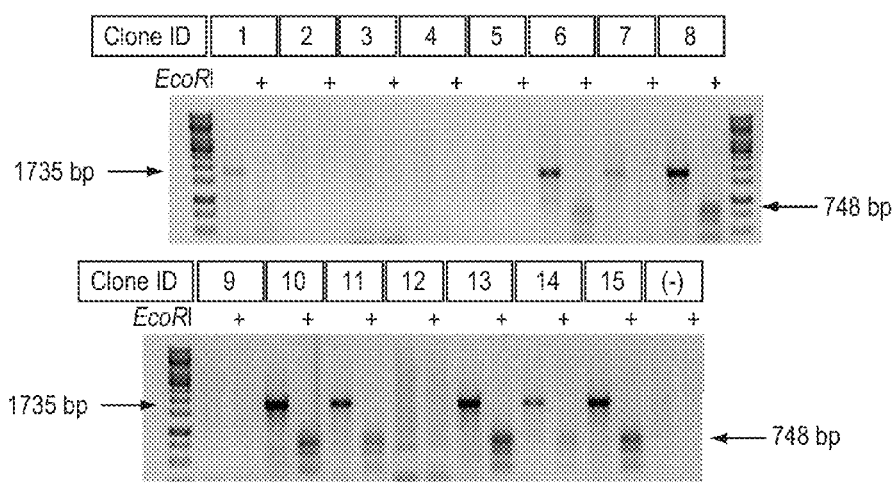
Figure 4:
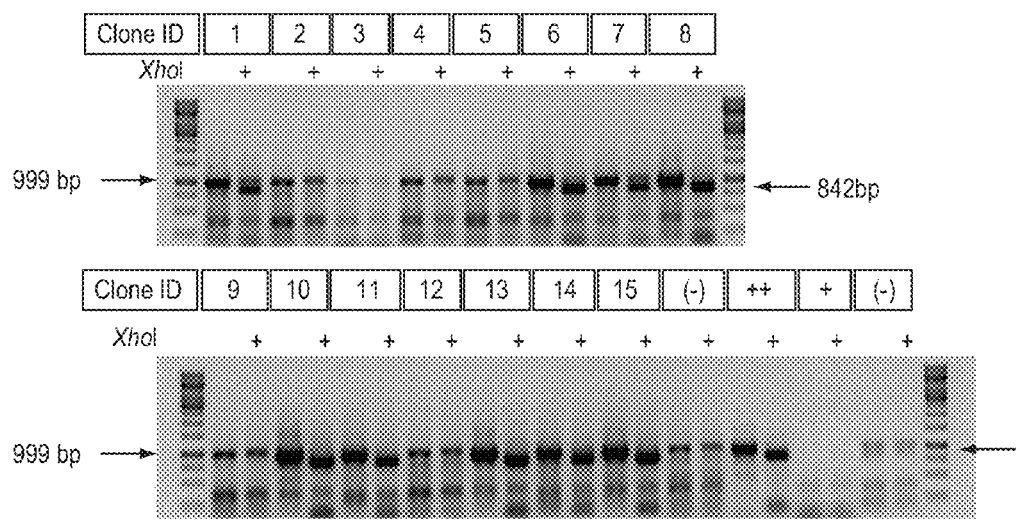

FIG. 4: Confirmation of round 1 and 3 positives by PCR/Restriction analysis. Panel (A) shows a correctly targeted (Targeted) LDLR locus at exon 4 after homologous recombination with the rAAV-LDLR E4 stop cassette. PCR primers for screening 5' (open triangles) and 3' (filled triangles) junctions are shown. Panel (B) depicts 5' junction PCR performed on WGA DNA from 7 and 8 colonies identified in the primary PCR screen of round 1 and 3, respectively. PCR from correctly targeted clones was expected to produce the 1735 bp and its identity is verified by restriction digest with EcoRI (labeled "E" in panel A) resulting in 3 fragments (748, 607 and 380 bp) of which the 748 bp band is indicated. WGA DNA from a negative colony was used as the negative control (−). Panel (C) depicts 3' PCR from correctly targeted colonies that produced a band of 999 bp and with its identity as verified by restriction digest with XhoI resulting in 2 fragments of 842 (indicated) and 157 bp. Two positive (++~150 copies, +15 copies) and two negative controls (WGA DNA from a negative colony) are shown. While a band appears in both negative controls at approximately 999 bp, it is not cleaved by XhoI indicating amplification of a random DNA fragment of similar size rather than a positive result. This feature can also be observed in clones 2-5, 9 and 12. The PCR was not sensitive enough to detect the 15 copy positive (+) control.

Figure 5:
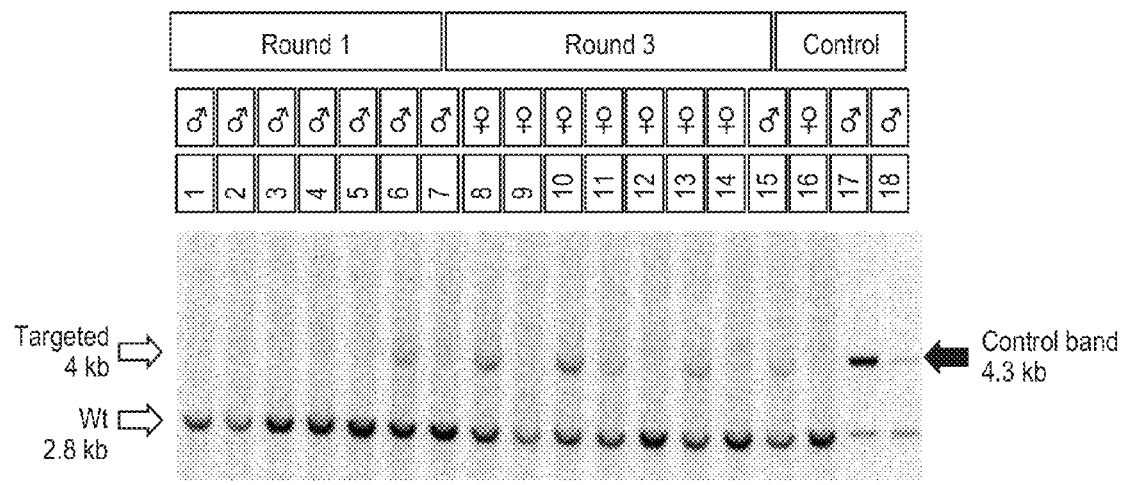

FIG. 5: Confirmation of round 1 and 3 positives by Southern Blotting: Candidates identified by PCR (FIG. 4) were subjected to WGA/Southern blotting. Restriction digest with EcoRI releases a fragment of 2.8 kb in wild type (Wt) cells and a 4.0 kb fragment for correctly targeted (Targeted) cells (see FIG. 1 for schematic). Each colony identified confirmed positive by 5' and 3' junction PCR (FIG. 4) displayed signal characteristic of a correctly targeted clone. Some variation in signal indicates not all colonies are pure, however, clones 8, 10, 13 and 15 appear to contain a majority of heterozygous LDLR knockout cells.

Figure 6:
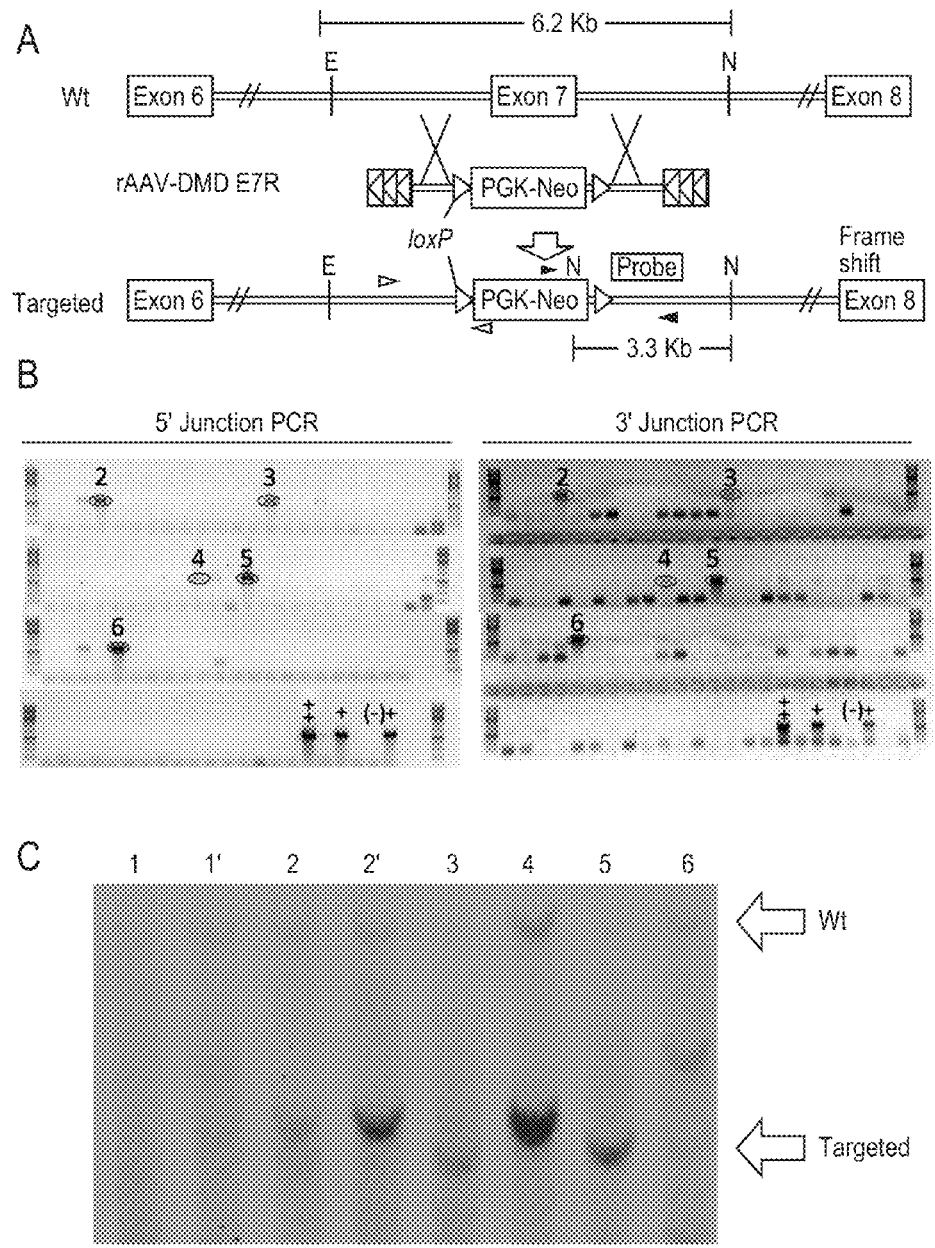

FIG. 6: DMD Exon 7 Replacement. Panel (A) is a schematic that shows both wild type (Wt) and a correctly targeted (Targeted) DMD locus at exon 7 after homologous recombination with the rAAV-DMD E7R replacement cassette. The rAAV-DMD E7R cassette contains a foxed PGK-Neo selection cassette flanked by approximately 1 kb homology arms upstream and downstream of exon 7. Homologous recombination between the DMD locus and rAAV-DMD E7R will result in the complete ablation of exon 7 and a frame shift in the full length dystrophin isoform. Panel (B) shows that G-418 resistant colonies were screened for gene targeting by amplification of junctions between the DMD locus and the PGK-Neo cassette. Both 5' and 3' junctions could be detected with separate primer pairs (panel A) 5' primers open triangles, 3' primers filled triangles, allowing for confirmation of replacement rather than insertion at exon 7. Several positive signals are observed for both the 5' and 3' ends, often from identical wells confirming the presence of correctly targeted cells. Both positive (++3,000 copies, +30 copies) and negative (−wild type genomic DNA only) controls are shown in the bottom right corner of each gel. Panel (C) shows candidates identified by PCR (panel B) and subjected to WGA/Southern blotting. Clones correspond to the numbering in panel (B) (clone 1 not shown), and lanes labeled 1' and 2' are simply replicates created with half volume WGA reactions. Restriction digest with EcoRI and NcoI (indicated as "E" and "N" in panel A respectively) will release a fragment of 6.2 kb in wild type cells and a 3.3 kb fragment for correctly targeted cells. The strong band observed in for wells 1, 2 and 4 above the 3.3 kb "targeted" band is the predicted size of head to tail concatemers of the rAAV-DMD E7R construct. Each well contains at some signal at 3.3 kb while wells 3 and 5 contain mostly targeted cells.

Figure 7:
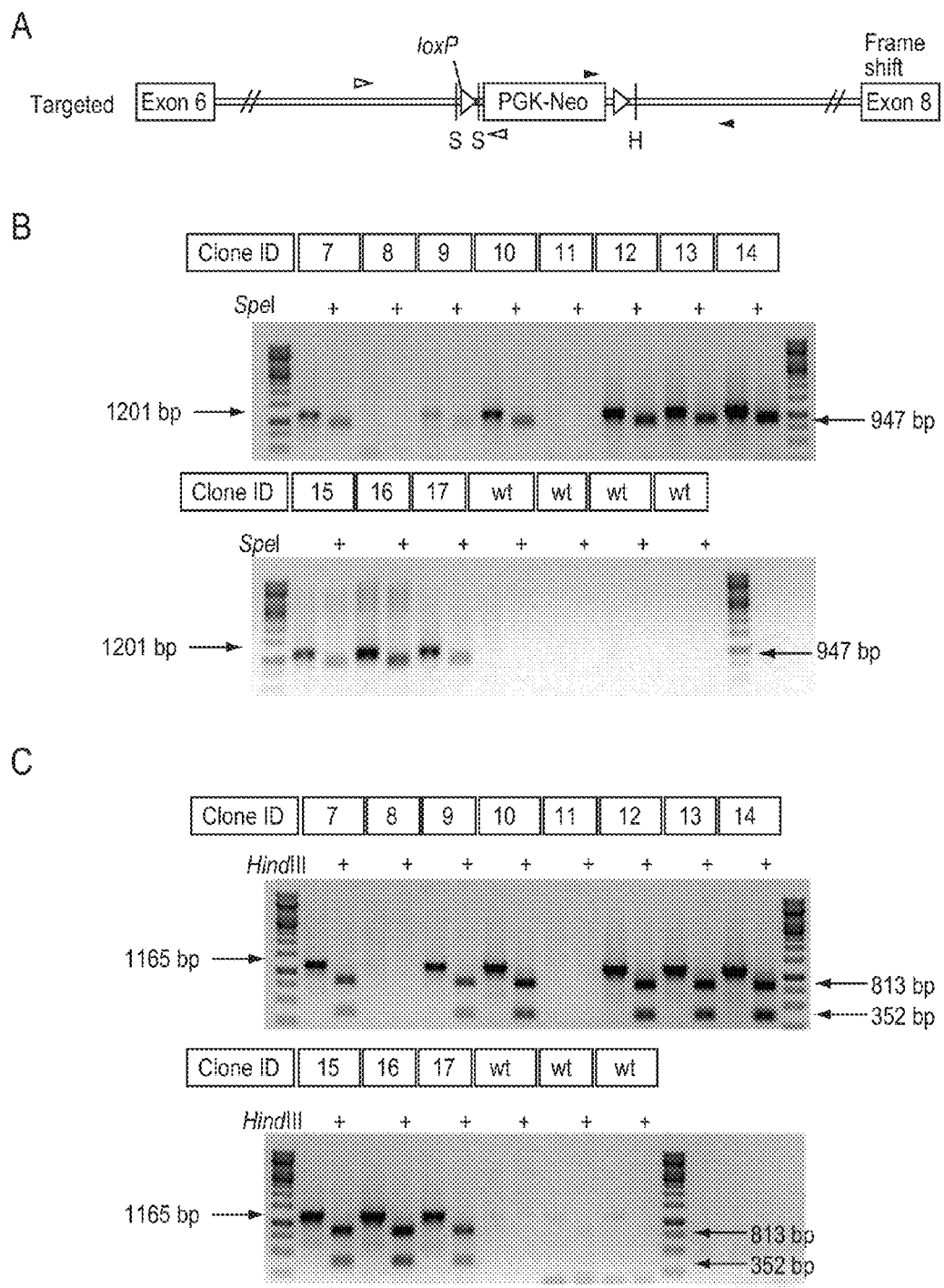

FIG. 7: Confirmation of round 2 positives by PCR/Restriction analysis: The panel (A) schematic shows a correctly targeted (Targeted) dystrophin locus at exon 7 after homologous recombination with the rAAV-DMD E7R replacement cassette. PCR primers for screening 5' (open triangles) and 3' (filled triangles) junctions are shown. Panel (B) shows a 5' junction PCR that was performed on WGA DNA from 11 colonies identified in the primary PCR screen. PCR from correctly targeted clones will produce the expected 1201 bp and its identity is verified by restriction digest with SpeI (labeled "S" in panel A) resulting in 3 fragments of which the 947 bp band is indicated. Eleven male colonies (7-16) and one female colony (17) are shown. (C) 3' PCR from correctly targeted colonies produces a band of 1165 bp and its identity is verified by restriction digest with HindIII resulting in 2 fragments of 813 and 352 bp. Eleven male colonies (7-16) and one female colony (17) are shown.

Figure 8:
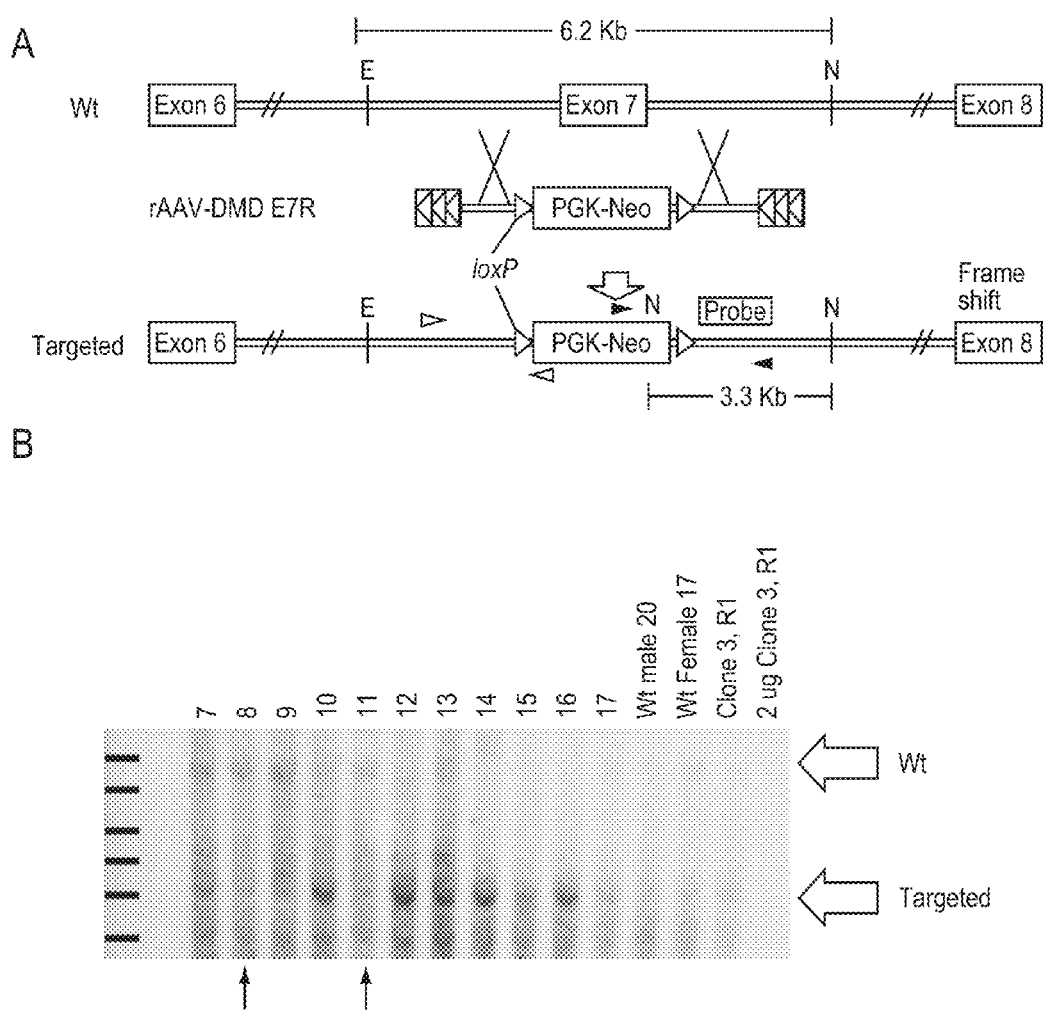

FIG. 8: Confirmation of round 2 positives by Southern Blotting. Panel (A) is a schematic of gene targeting at exon 7 of the DYSTROPHIN locus. Panel (B) shows results for candidates identified by PCR (FIG. 7) and subjected to WGA/Southern blotting. Eleven male colonies (7-16) and one female colony (17) are shown. Restriction digest with EcoRI and NcoI (indicated as "E" and "N" in panel A respectively) will release a fragment of 6.2 kb in wild type cells and a 3.3 kb fragment for correctly targeted cells. Each colony, with the exception of 8 and 11 (indicated with arrows) gave positive signal for both 5' and 3' junctions.

Figure 9:
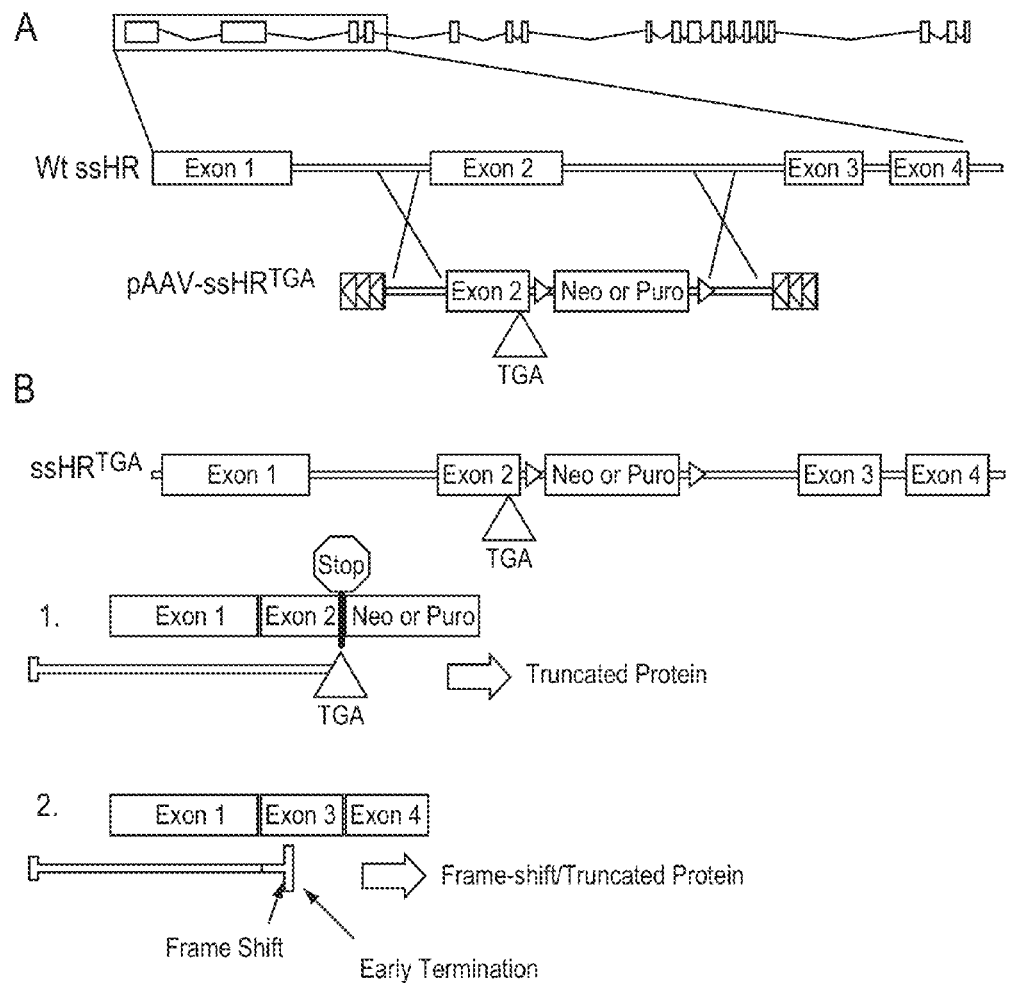

FIG. 9: The porcine Hairless gene (HR) and knockout strategy. (A) The wild type (Wt) HR gene is comprised of 18 exons, and is located on chromosome 14. The area surrounding exon 2 is highlighted and enlarged. A premature stop codon (TGA) was introduced into exon 2 by rAAV-Homologous recombination to ablate full length HR protein in pigs by truncation of the protein. The pAAV-HR$^{TGA}$ vector includes the majority of exon 2 and homology arms both up and downstream of exon 2. For selection of targeted cells, two version of the HR$^{TGA}$ have been constructed, one with a neomycin (Neo) resistance cassette, another with a puromycin (Puro) resistance cassette. Panel (B): This schematic shows the structure of the targeted HR$^{TGA}$ allele. The HR$^{TGA}$ allele will interfere with full length HR production in two ways; 1) translation will be terminated at the engineered TGA stop codon 2) skipping of exon 3 by alternative splicing between exons 1 and 3 will cause a frame shift mutation.

FIG. 10: LDLR Partial CDS from MARC library est sequenced by Applicant. (SEQ ID NO:1).

FIG. 11: LDLR HinDIII Subclone sequence (includes exons 2-5). (SEQ ID NO:2).

DETAILED DESCRIPTION

One embodiment of the invention is a method of transfecting an artiodactyl cell. A first group of artiodactyl cells may be treated to introduce an exogenous gene and then mixed with a second group of artiodactyl cells that have not been so treated. This process has been observed to produce significant efficiencies and reproducibility. A series of working examples are set forth below, followed by a more detailed overview of this embodiment.

The working examples are also embodiments of the invention. These examples describe stably transfected swine cells made with various transformations. These cells may be used to make transgenic animals, which are useful for many purposes including animal models of human diseases and conditions and sources of tissue.

Hypercholesterolemia Swine Model: Transgenic Pigs with LDLR Gene Modification

Cardiovascular disease is a leading cause of death and dysfunction in the United States, with coronary artery disease being a major contributor. Animal models are fundamental to understanding the mechanisms of atherosclerosis. The development of new therapies relies heavily on the use of these models. Unfortunately, there is a lack of suitable large-animal models for studying new therapies or testing them. For instance, several stent-drug combinations have been successful in animal studies but failed in subsequent human clinical trials. Trials that are successful in the animal models that subsequently fail in human trials may be explained by unfaithful replication of human disease pathology in the animal models.

Hypercholesterolemia is a principal cause of atherosclerosis. Rabbits, swine and rhesus monkeys with genetic mutations linked to hypercholesterolemia have been used to study atherosclerosis and recent research has focused on genetically modified mice. However, genetically modified mice that manifest hypercholesterolemia do not exhibit lesions typical of atherosclerosis in humans. Some inbred swine with defective Low-Density Lipoprotein Receptors (LDLR) do develop lesions but do not show a consistent and predictable manifestation of the disease. The Low-Density Lipoprotein Receptor (LDLR) is a cell surface receptor that mediates the endocytosis of cholesterol-rich low density lipoprotein (LDL). In humans, the LDLR protein is encoded by the LDLR gene and was implicated as having a role in familial hypercholesterolemia (Brown M S, Goldstein J L (1984). "How LDL Receptors Influence Cholesterol and Atherosclerosis". Scientific American 251: 52-60.).

Figure 1:
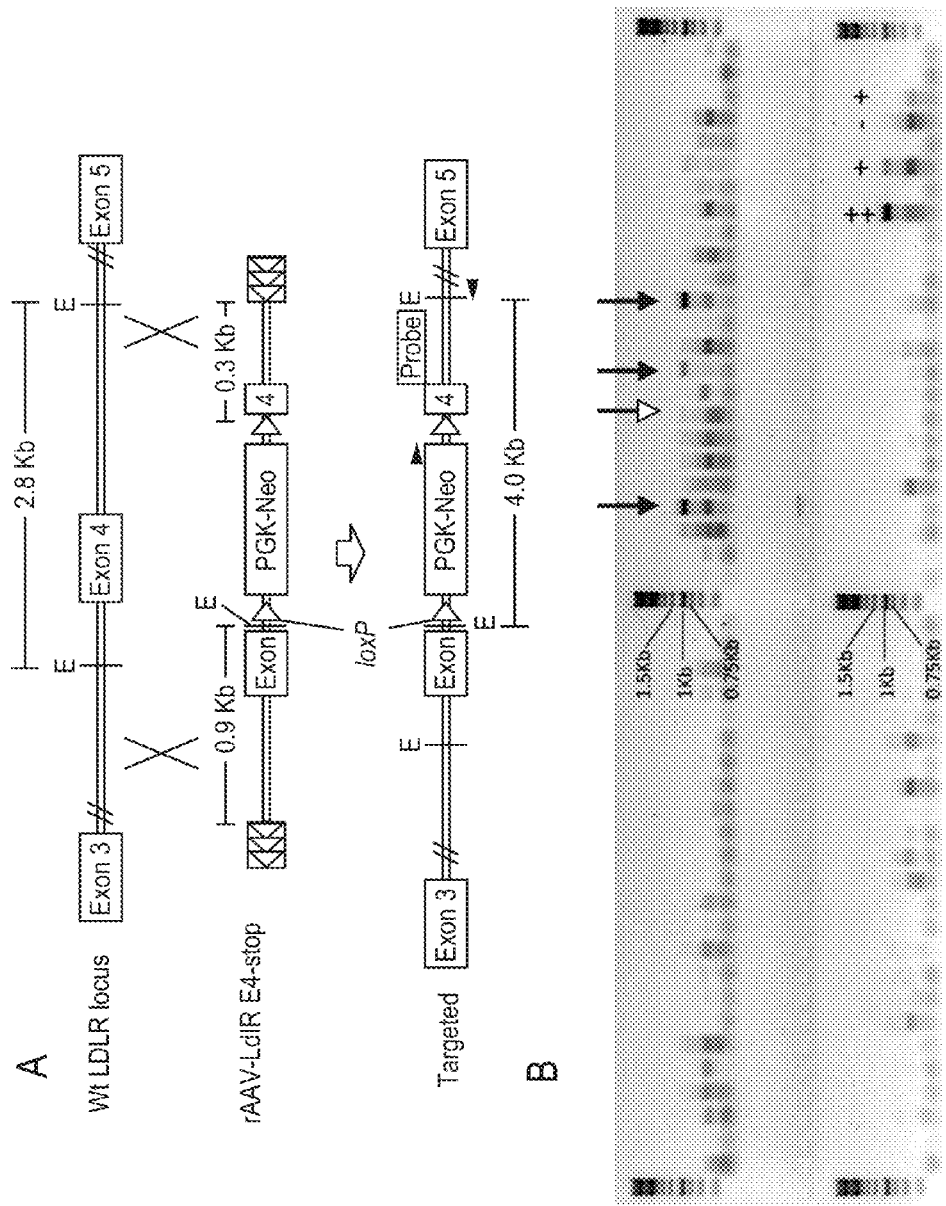
FIG. 1 depicts the LDLR knockout strategy and PCR results. Panel A: Schematic of wildtype (wt) and correctly targeted (Targeted) LDLR locus at exon 4 after homologous recombination with the rAAV-LDLR E4-stop replacement cassette. The rAAV-LDLR E4-stop cassette contains a floxed PGK-Neo selection cassette inserted within exon 4 flanked by a 5' homology arm of 0.9 kb and a 3' homology arm of 0.3 kb. Panel (B) G-418 resistant colonies were screened for gene targeting by amplification of junctions between the LDLR locus and the PGK-Neo cassette (indicated as black triangles in panel A). Shown is the PCR result from one of the 25 µl transduction plates. Positive wells are expected to have a 1.1 Kb PCR product whereas negative colonies should have no product. Examples of strong (black arrows) and weak signal (light arrows) are shown. Positive (++~150 copies, +15 copies) and negative (–wild type genomic DNA only) controls are shown in the bottom right corner of the gel.

Herein, as described below, transgenic swine cells were made with a defect in LDLR expression. Transgenic animals may be made from these cells using any of a variety of standard technique known to artisans in these fields. In brief, the production of a functional LDLR gene product was disrupted by introduction of a stop cassette within LDLR exon 4 by Adeno-associated virus (rAAV) homologous recombination (HR). An rAAV HR cassette (rAAV-LDLR-E4-stop) was generated with a PGK-Neo selection cassette inserted within LDLR exon 4 at the XhoI restriction site (FIG. 1). Replacement of LDLR exon 4 with rAAV-LDLR-E4-stop resulted in a truncated, non-functional LDLR protein product. Several AAV constructs were designed and created that either targeted other exons or that avoided certain repetitive elements around exon 4. Colonies with LDLR nonexpression were identified from three separate transductions.

First Transduction Results

Two million male primary fetal fibroblasts (PFF) were plated in each well of a 6-well plate 24 hours prior to incubation (completely confluent) with 5, 25, 100, and 150 µl (per well) of rAAV-LDLR-E4-stop viral supernatant in 1 ml of growth medium. Cells were incubated for two hours prior to the addition of 3 ml growth medium. Twenty-four hours later, cells from each transduction were plated onto five 96-well plates at the density of 2000 cells/well. Cells were allowed to recover overnight prior to selection in medium containing 250 µg/ml G418, subsequently increased to 300 µg/ml on day 8. On day 16, all the wells were 100% confluent from the 100 an 150 µl transductions, most wells were completely confluent from the 25 µl transduction, and approximately half of the wells from the 5 µl transduction were confluent. On day 17, cells were trypsinized from both 5 and 25 µl transduction plates with 25 µl of TRYPLE EXPRESS (Invitrogen, CA) for 5 min under 37 degrees Celsius after Phosphate Buffer Solution (PBS) washing. 175 µl of serum containing media were added and mixed. Half of the cell suspension was cryopreserved in deep-well plates while the remaining half was transferred to 96-well PCR plates, pelleted and resuspended in 20 µl of 1×PCR lysis buffer.

Second Transduction Results

The second transduction was performed as with the first transduction with a few exceptions, as follows. PFF cells were plated on 6-well plates 24 hours prior to transduction to achieve a density of 30% confluence. Twenty-five microliters of rAAV-LDLR E4-stop viral supernatant was added to 1 ml growth medium and were plated onto five 96-well plates at the density of 1,000 cells/well 24 hours later. Cells were allowed to recover overnight prior to selection in medium containing 300 ug/ml G418. On day 15, most wells were 100% confluent and cells were split and plated on replicate 96-well plate wells. When wells were 100% confluent, cells from one replicate were collected in 1×PCR lysis buffer.

PCR Analysis

PCR analysis was conducted on the 5 µl and 25 µl transduction plates from the first transduction and the 25 µl transduction plates from the second transduction using primers designed to amplify across the 3' junction (FIG. 1 Panel A). Approximately 50% of wells were confluent in the first transduction 5 µl transduction plates, therefore, it would be expected that most wells would harbor one G-418 resistant colony. Unfortunately, no positive wells were detected from the 5 µl plates suggesting that homologous recombination at the LDLR locus had occurred in less than 1 in 250 G-418 resistant colonies.

Figure 2:
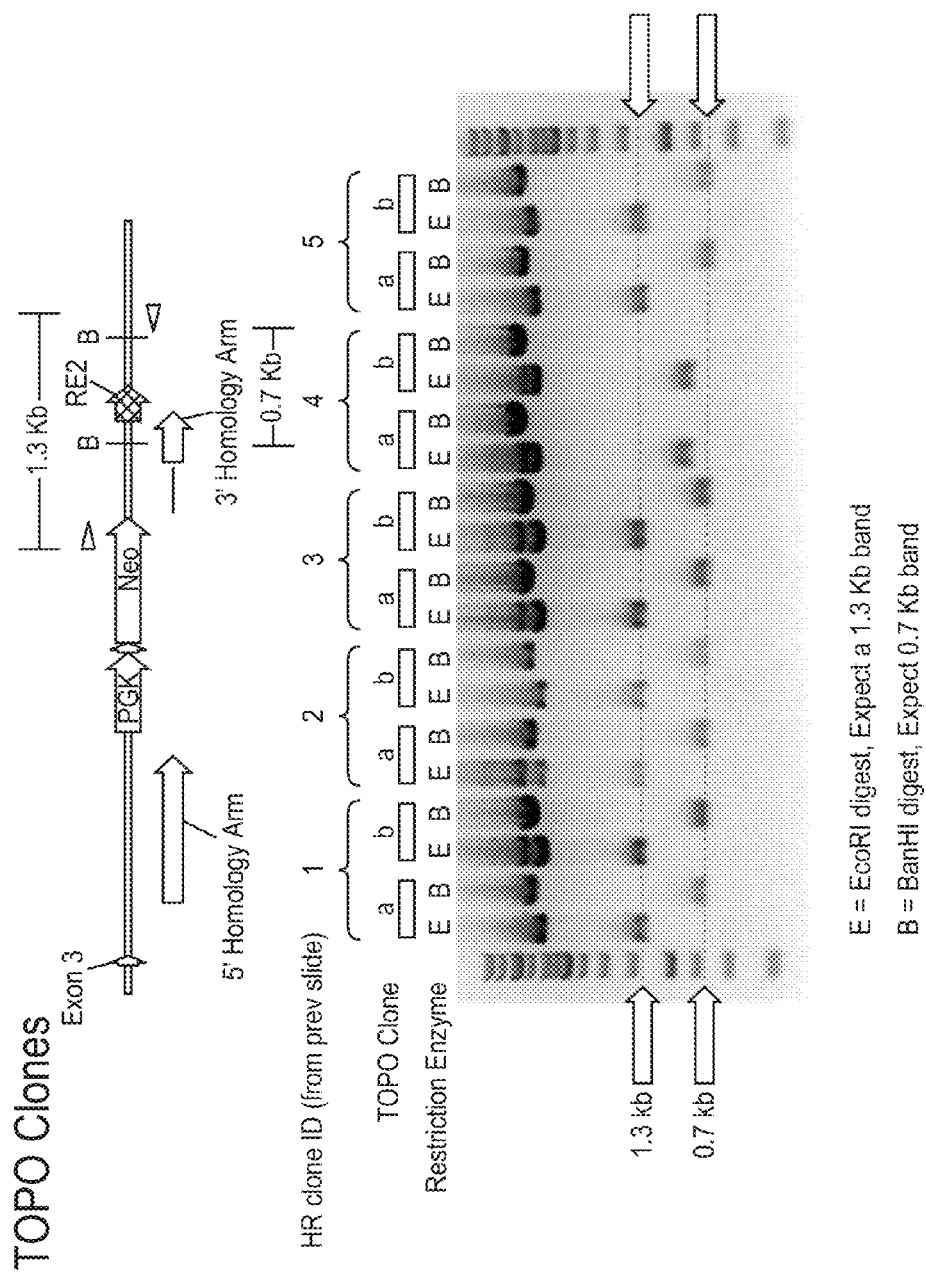
FIG. 2 depicts the restriction analysis of the 3'-end of recombinant amplicons in the strategy of FIG. 1. A second set of PCR primers (blue and red triangle) also confirmed accurate targeting at the LDLR locus. PCR amplicons were TOPO-cloned and subjected to restriction analysis and sequencing (data not shown) to confirm homology recombination. The liberation of a 0.7 Kb band from clones 1, 2, 3, and 5 confirmed the identity of the recombinant colonies.
Figure 3:
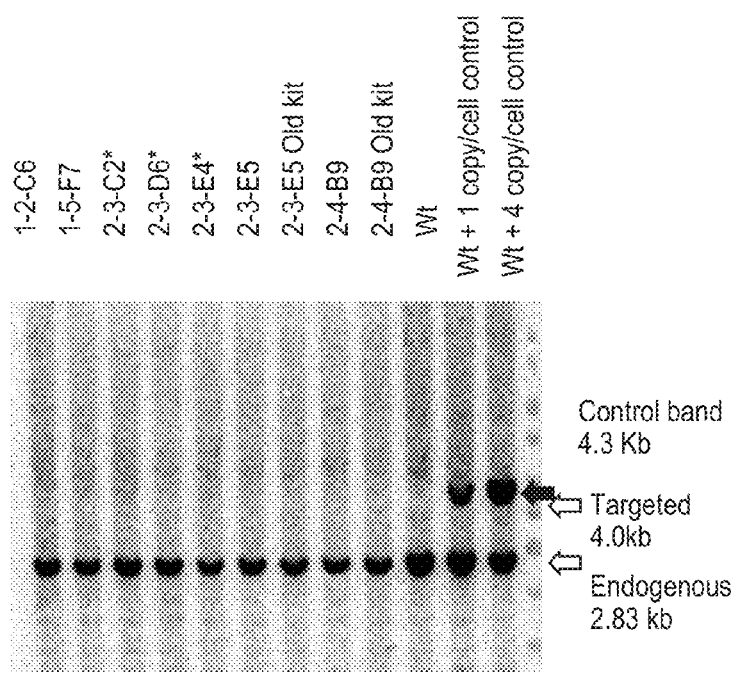
FIG. 3 depicts the results of a Southern analysis of recombinant colonies. Eight colonies amplified by WGA were subjected to Southern analysis with the probe indicated in FIG. 1 panel A. The expected endogenous (E), positive control (+), and targeted band (clones marked with a asterisk) were observed, although the majority (~80%) of cells appear in each clone appear to be wild type.

Cells from the first transduction and second transduction 25 µl transduction plates were screened next. Unlike the previous first transduction 5 µl plates, most wells were 100% confluent and were expected to contain 2-6 independent G-418 resistant colonies per well. Despite the likelihood of multiple colonies per well, positive signals from 26 wells of the first transduction and 15 wells of the second transduction (FIG. 1 panel B) were detected. Signal intensity of the PCR varied significantly among positives and likely reflected the proportion of cells that are correctly targeted versus resistant "bystander" colonies containing random integration of the targeting vector. In total, 11 of the 41 positives had strong signal and were cryopreserved for WGA/Southern blot analysis. PCR products from 4 of 5 of the strong positives were confirmed by restriction digestion (FIG. 2). These clones were further analyzed by Southern hybridization (FIG. 3) and identified the expected band for the correctly targeted locus. However, in pure knockout colonies, a 50:50 ratio of intensity between knockout and wild type alleles were expected, thus clones with the expected knockout allele appear to be confounded by the presence of wt cells, ~80% based on signal intensity (FIG. 3).

Third Transduction for LDLR Disruption

A third infection was conducted in both male and female PFF. Transduced cells were plated at densities of 100/well, 200/well, and 500/well on 96-well plates (5 replicates for each density and sex), supplemented with wild type cells to a total of 1,000 cells per well, and selected in G-418 for two weeks. Neomycin resistant colonies appeared in approximately 30 to 50 of wells in the 100 and 200 plates while greater than 90 percent of wells in 500 plates contained a colony (Table 1). Primary PCR screening was performed on the 100 and 200 plates resulting in 2 and 11 positive wells for male and female cells respectively (Table 2). The healthy (1 male and 7 female) colonies were cryopreserved and a portion were set aside for WGA. PCR of both 5' and 3' junctions from WGA DNA revealed positive signal in 1 and 5 of the male and female colonies respectively (FIG. 4 and Table 2). Identity of the junction PCR was confirmed by restriction digest (FIG. 4). Finally, positive clones from both the first and second transductions were analyzed by Southern blotting confirming the knockout allele in each PCR positive clone (FIG. 5).

TABLE 1

96-well plate selection (Third transduction)

| Plating density (cells/well) | Wells | Wells w/ Cells (% wells) | Neo$^R$ Colonies (% selected) |
|---|---|---|---|
| 100 Male | 480 | 188 (39) | 188 (0.39) |
| 200 Male | 480 | 222 (46) | 222 (0.23) |
| 100 Female | 480 | 150 (31) | 150 (0.31) |
| 200 Female | 480 | 183 (38) | 183 (0.19) |

TABLE 2

Targeting Frequency (Third transduction)

| | Neo$^R$ Colonies (% selected) | 1° PCR Positives (% colonies) | 5'-3' PCR RE Positives (% colonies) | Frequency (HR positive/selected) |
|---|---|---|---|---|
| Male 20 | 410 (0.28) | 2 (0.48) | 1 (0.24) | $6.94 \times 10^{-6}$ |
| Female 17 | 333 (0.23) | 9 (2.7) | 5 (3.78) | $3.47 \times 10^{-5}$ |

These tests verified that cells were made with LDLR knockouts. Specifically, the following clones contained cells with heterozygous knockout of the LDLR locus; M: clone 1 & F: clones 8, 10, 11, 13, 14, and 15. In addition, the male clones 1 and 7 may contain the knockout, but failed to be verified by WGA: Southern analysis. The cells may be cloned into male and female pigs by Somatic Cell nuclear transfer, Chromatin transfer or other suitable techniques. These founders may then be bred to create pigs homozygous for knockout of the LDLR gene.

These techniques may be used to produce animals that are homozygous or heterozygous for the disrupted gene; cells that have a marker gene or are free of a marker gene, a swine that exhibits a phenotype chosen from the group consisting of hypercholesterolemia, atherosclerosis, and atherosclerotic lesions (including any combination thereof), wherein the disrupted LDLR gene is disrupted at exon 4, and wherein all of the LDLR genes in the swine are disrupted.

For this gene and others, techniques for making marker-free recombinant cells and animals has been described in U.S. Publication No. 2010/0146655, which is hereby incorporated herein by reference for all purposes; in case of conflict, the specification is controlling.

The working example described these process with respect to disruption of exon 4 of LDLR. Familial hypercholestolemia via LDLR mutation is commonly due to a dominant mutation in LDLR at a variety of locations ranging from exon 1 to deletion in the final three exons (as is known, see LOW DENSITY LIPOPROTEIN RECEPTOR; LDLR-OMIM, hereby incorporated by reference herein). Therefore, frameshift mutation, truncation, or introduction of single amino acid changes throughout the LDLR gene are expected to disrupt LDLR function. Targeting such changes would simply require the acquisition of the pig LDLR sequences available in Genbank, ENSEMBL, or as described in SEQ ID NO:1, and the application of methods for homologous recombination, allele conversion, or the introduction of an indel using zinc finger nucleases, meganucleases, or TAL effector nucleases or any other targeted method for DNA breakage/modification. Like humans, pigs have been described with dyslipidemia on the basis of mutations in components of the lipid scavenging system. For example, all pig breeds examined are monomorphic at positions in the apolipoprotein E (ApoE) gene that are associated with a predisposition for high plasma LDL-cholesterol in patients, i.e., they encode arginine residues at positions 112 and 158 that correspond to the deleterious ApoE4 isoform. Rapacz identified "naturally" occurring hypercholesterolemia in farm pigs leading to atherosclerotic plaques in aged pigs. The causative mutations were identified in two familial hypercholesterolemic pig lines including an alternative apolipoprotein B (ApoB) allele and a missense mutation in exon 4 of the low density lipoprotein receptor (LDLR) (R84c). Mutations at the analogous residue in human LDLR(R115c and R115H) have been reported, the latter displaying 64% LDL clearance activity compared to wild type LDLR in an in-vitro study. This suggests that the R84c mutation in pigs is likely to be a hypomorphic allele of LDLR. As in humans, pig are dependent on LDLR-mediated removal of LDL from circulation since they do not produce ApoB-48 in their livers to allow for ApoE dependent removal of LDL via the chylomicron remnant receptors, as is the case for rodents and dogs. Ossabaw pigs are an animal model of hypercholesterolemia; while useful, genetic engineering of LDDR defects in this breed and others will be have a number of advantages for improving these models. One advantage is a severe and rapid onset of dyslipidemia, considering the conservation of LDLR in pigs and humans, as well as the predicted predisposition to high plasma LDL-cholesterol. The motifs known for truncating, ablating, or otherwise disrupting LDDR in swine, humans, and mice may accordingly be applied in the creation of a transfected cell and a transgenic swine.

SEQ ID NO:1 was used to generate a probe for BAC library screening and recovery of a genomic clone containing the pig LDLR gene. SEQ ID NO:2 is a HinD III subclone from the LDLR BAC that encompasses exons 2-5. Once available, this sequence was verified by comparison to GenBank: FP102365.2.

Further disclosure relating to lipoprotein receptors is provided in U.S. Pat. Nos. 5,521,071, 5,798,209, 6,174,527, 6,833,240, 7,008,776, 7,306,794, 7,416,849 and U.S. Publication No. 2002/0155446 which are hereby incorporated herein by reference for all purposes; in case of conflict, the instant specification is controlling.

Muscular Dystrophy Swine Model: Transgenic Pigs with Dystrophin Gene Modification The primary product of the Dystrophin gene in muscle is dystrophin, a 427 kDa rod-shaped protein having four domains: an N-terminal actin binding domain, 24 triple helix spectrin-like repeats with four hinge regions, a cysteine-rich domain with two potential calcium binding motifs, and a unique C-terminal domain (Koenig et al.). In muscle, dystrophin forms a linkage between the cytoskeletal actin and a group of membrane proteins, as well as with a number of non-membranal proteins (collectively called dystrophin associated proteins; DAPs) (Yoshida et al., Ervasti et al.). The N-terminal domain binds to the cytoskeletal actin and the association with the DAPs is mediated mainly by the cysteine-rich and C-terminal domains of dystrophin (Suzuki et al., Jung et al.). One of the DAPs, α-dystroglycan, binds laminin. Thus, in muscle, this complex links the cytoskeleton, the sarcolemma and the extracellular matrix (Ahn et al., Campbell, Ozawa et al.).

The Dystrophin gene also codes for two non-muscle isoforms of dystrophin, each controlled by a different promoter located in the 5' end region of the gene; the brain type dystrophin (Nudel et al., Barnea et al., Boyce et al.) and Purkinje cell type dystrophin (Gorecki et al.). In addition, internal promoters located within downstream introns for the dystrophin gene regulate the expression of smaller products. Dp71, a 70.8 kDa protein, consists of only the cysteine-rich and C-terminal domains of dystrophin (Bar et al., Lederfein et al.). It is the most abundant non-muscle product of the dystrophin gene and has been found in all tissues tested so far except for differentiated skeletal muscle. The highest levels of Dp71 are found in the brain (Rapaport et al., Greenberg et al.). The other known small products of the dystrophin gene consist of the cysteine-rich and C-terminal domains with various extensions into the spectrin-like repeats domain. These products are: Dp116 (Byers et al.), Dp140 (Lidov et al.), and Dp260 (D'Souza et al.), which are expressed mainly in Schwann cells, brain, and retina, respectively, and have molecular weights of 116, 140 and 260 kDa. The functions of the non-muscle dystrophins and of the smaller products of the dystrophin gene are not known.

Rodent models of dystrophin have proven invaluable in defining the complexity of muscle disease, and enabled the development of several promising therapeutic strategies for DMD. However, muscle degeneration in the mdx mouse model is mild in comparison to DMD patients. For instance, mdx mice are mobile, they do not have significant fibrosis or joint contractures, and the skeletal myofibers are only partially replaced by adipose cells later in life. The myotendinous junctions are severely impaired in DMD patients (Bell, C. D. and Conen, Hasegawa et al., Nagao et al.), but only have minor alterations in maturation and maintenance in mdx mice (Law and Tidbal). In addition, the loss of synaptic folds in the neuromuscular synapse has little effect on synaptic transmission in mdx mice (Banks et al., Carlson et al., Lyons et al.), but has a greater effect in DMD patients (Slater). Furthermore, the lifespan of mdx mice are only moderately shortened (~20%) so the relevance of different therapeutic strategies is difficult to assess (Chamberlain et al.). Therapeutic strategies may instead benefit from examining large animal models of DMD.

One explanation for the mild phenotype of mdx mice is that the functional requirement of dystrophin to transmit muscle forces may be minimal given their small and weak stature in comparison to humans. Satellite cells also retain their regenerative potential better in mdx mice than in DMD patients, so may more actively repair damaged tissue. Another possibility is that homologous proteins (such as utrophin) can compensate more effectively for the absence of dystrophin in mice. Consistent with this hypothesis, two independent laboratories generated mice lacking both dystrophin and utrophin to generate a more severe model of DMD (Deconinck et al., Grady et al.). mdx:utrn −/− mice are smaller than wild-type mice, develop severe kyphosis, and become less mobile with age (Deconinck et al., Grady et al.) and they develop an inflammatory response in the skeletal musculature (Deconinck et al., Grady et al. In these double knockout mice, many of the muscle fibers are replaced by fibrotic tissue that contributes to joint contractures (Deconinck et al., Grady et al.). However, clear differences in the size, stem cell dynamics, and requirement for dystrophin function argue against the continued reliance on rodent models.

There are several cxmd dog models of DMD, including the Golden Retriever (GRMD) (Cooper et al.), Rottweiler (Partridge) German Short-Haired Pointer (Schatzberg), and cxmdj Beagles in Japan (Shimatsu et al.). These various dogs display similar although variable phenotypes (Polejaeva, Wheeler and Walters). There is a high mortality rate of early neonatal GRMD dogs from selective muscle degeneration (Charreau et al., Kuroiwa et al.). For dogs that live through the neonatal period, muscle degeneration is followed by muscle regeneration and a large inflammatory response (Nguyen et al.). Some of the muscles have high concentrations of crystalline calcium and hyaline (Cooper et al., Nguyen et al.) and muscle fibers begin to be replaced by fibrotic tissue and adipose cells at approximately 2 months of age (Nguyen et al.). Joint contractures are prominent by 6 months and mobility is severely impaired. The muscles are atrophic, weaker, and more susceptible to contraction-induced injury (Nguyen et al., Childers et al.). GRMD dogs develop cardiomyopathy (Chetboul and Carlos, et al., Chetboul and Escriou et al.) and respiratory distress that can lead to death (Valentine et al., 1991). GRMD dogs display a mosaic expression of truncated dystrophins with deletions from exons 2-10 and 4-13 (Schatzberg et al.), although expression becomes somewhat more uniform with age (Cooper et al.). These truncated dystrophins lack part of the N-terminal actin binding domain, hinge 1, spectrin repeat 1, and part of spectrin repeat 2. The N-terminal actin-binding domain of dystrophin is important for dystrophin expression and function (Banks et al., Beggs et al., Le et al., Chelley et al., Le et al., Matsumra et al., Muntoni et al., Novakic et al., Prior et al., Takeshima et al., Winnard et al.).

Although these dogs sometimes present a faithful model of DMD, there is significant phenotypic variability between dogs with the same mutation (Cooper et al., Shimatsu et al. 2003). In human patients and the GRMD model, dystrophin expression can be restored when there is a point mutation in the N-terminal actin binding domain (Schatzberg et al., Winnard et al.). Although these regions are important for dystrophin expression and function, the central actin-binding domain can partially compensate for deletions in the N-terminal actin-binding domain (Warner et al., Rybakova et al.). Dp260 can mitigate muscle degeneration when expression levels are near normal (Warner et al.). Thus, variations in expression of the truncated dystrophins in the dog model could explain the variability in phenotype between dogs. Despite being the only large animal model of DMD, the use of dogs is expensive; they are not susceptible to genetic manipulation, and are not a preferred system due to the fact that they are an emotive species.

Herein are described cells for making genetically engineered pigs to provide a superior large animal model of DMD. The size, musculoskeletal and heart physiology of pigs is remarkably similar to humans. The latter fact underlies the widespread use of pigs in cardiovascular research. The size of the pig is will elicit mechanical strain sufficient to induce DMD in the context of dystrophin deficiency. In addition, the high reproductive rate (averaging 10 piglets per litter), and genome malleability due to cloning put pigs as a large animal model on par with rodents but with greater anatomical and physiological similarity to humans. Use of gene knockout technology as described herein provides a more robust model.

This method is described in detail herein in the context of the production of swine cells with a knockout for the dystrophin gene in male and female domestic and miniature swine cells. These cells may be used in nuclear transfer to produce DMD −/+founder animals that are bred and expanded through breeding and then used to meet a growing need of medical device and pharmaceutical companies for uniform animal models of human pathologies that can help predict the outcome of human therapeutic interventions.

Establishment of pigs ablated at the dystrophin locus has been undertaken in both male and female cells. Cloning male cells into pigs by somatic cell nuclear transfer may be used to generate founders that have DMD, permitting rapid evaluation of the suitability of pigs as a model. Propagation of pigs ablated at the dystrophin locus may be undertaken using females given its location on the X chromosome. Sows as viable founders will maintain one normal copy of dystrophin and would then need to be bred to generate males with DMD. The results herein showed a successful process for knocking out the dystrophin gene in male and female fibroblasts. These cells are a suitable resource for Somatic cell nuclear transfer or chromatin transfer and will be used to create founders.

The porcine dystrophin gene was disrupted by recombinant Adeno-associated virus (rAAV) homologous recombination to produce a model of muscular dystrophy in swine. Homologous recombination between the rAAV cassette and the dystrophin gene would result in the replacement of exon 7 with a PGK-Neo selection cassette (FIG. 6). The absence of exon 7 creates a frame shift in the full length dystrophin transcript eliminating the production of the Dp427 dystrophin isoform.

The experimental approach involved creation of a rAAV replacement cassette (rAAV-DMD E7R) for targeting of DMD exon 7 using a fusion PCR technique described in Kohil et al., 2004 (FIG. 6 Panel A). Viral packaging was conducted by co-transfection of AAV-293 cells with plasmids: rAAV-DMD E7R, pAAV-RC, and pAAV-helper. Two days after transfection, cells from one 100 mm plate were lysed in 1 ml of growth media by 3× freeze thaw cycles and stored at −80° C. in 300 microliter aliquots.

Viral Transduction Methods:

Early passage pig fetal fibroblasts (PFF) were plated at a density of 30,000 cells/cm$^2$ in a single well of a six-well plate to achieve 70-80% confluence within 24 hours. Media was changed 1 hour prior to transduction and replaced with 1 ml of fresh growth medium. One hundred-fifty microliters of viral lysate was added to a single well and incubated under standard growing conditions. After a 24 hour incubation, cells were washed 3× with PBS, trypsinized and plated onto 96 well plates at densities ranging from 250 cells/well to 2,000 cells/well. Plates seeded at low density were adjusted to 1,000 cells per well with wild type fibroblasts to enhance plating efficiency. On the following day, medium containing 300 μg/ml G-418 was added and changed 3× in the course of two weeks. The surface area in the 96-well plate in this and other experiments was about 0.33 cm$^2$ per well, so that a density of 1000 cells per well is equal to about 3,000 cells per cm$^2$, so that densities ranged from about 800 to about 6000 cells per cm$^2$.

PCR Screen Methods:

After two weeks of selection in G-418, cells were trypsinized and divided 50:50 between a 96-well PCR plate and a 96-well growth plate. Cells in the PCR plate were pelleted and resuspended in 25 μl of lysis buffer while the growth plate was returned to the incubator. PCR was conducted between the PGK-Neo cassette and primers located outside of both the 5' and 3' homology arms (FIG. 6 Panel B). PCR positive wells were allowed to grow to confluence prior to trypsinization followed by removal of cells for Whole Genome Amplification (WGA)/Southern blotting and cryopreservation.

Results; First Transduction:

Early passage PFF were cultured to 70-80% confluence prior to transduction with 150 microliters of viral lysate. Cells were trypsinized after 24 hours of incubation and plated on 6 wells of 96 well plates at densities indicated in Table 3. After 14 days of selection in G-418, very few viable cells remained in the wild type control wells while each well of the 1,000 and 2,000 cells/well plates contained resistant cells. Most wells in the 500 and 250 plates also contained resistant cells (Table 3) however, unlike the 1,000 and 2,000 had both partially confluent and empty wells were present. Based on the percentage of wells containing resistant cells in the 500 and 250 plates, we would expect a range of 2-6 and 1-3 independent colonies per well respectively. These plates were screened for correct targeting by PCR to obtain an estimate of gene targeting frequency for subsequent experiments. Using PCR primers to amplify both 5' and 3' junctions, a positive signal was observed in 6-10% of wells containing resistant cells (FIG. 6 Panel B and Table 4). Wells giving strong signal for both 5' and 3' junctions were harvested for cryopreservation and WGA/Southern blotting. Since the DMD (dystrophin) gene is on the X chromosome and the cells used for this experiment were male, a pure knockout clone is expected to completely lack the 6.2 kb wild type allele, while wells containing more than one independent resistant colony were likely to contain both the wild type and 3.3 kb targeted allele. Despite the likelihood for multiple colonies per well, cells from 2 of the 6 wells analyzed by Southern blotting (clones 3 and 5) appeared to contain mostly targeted alleles (FIG. 6 Panel B).

TABLE 3

96-well plate selection (First transduction)

| Plating density (cells/well) | # of plates | Empty wells # (% wells) | Partially confluent # (% wells) | 100% Confluent # (% wells) |
|---|---|---|---|---|
| 250 | 1 | 10 (10.4) | 54 (56.2) | 32 (33.3) |
| 500 | 2 | 3 (1.8) | 120 (71) | 45 (27) |
| 1,000 | 2 | 0 | Nd | nd |
| 2,000 | 1 | 0 | Nd | Nd |

TABLE 4

PCR positive wells: (First transduction)

| Plating density (cells/well) | 5' Junction # (% wells$^a$) | 3' Junction # (% wells$^a$) | Both # (% wells$^a$) |
|---|---|---|---|
| 250 | 9 (10.5) | 9 (10.5) | 8 (9.3) |
| 500 | 12 (7.2) | 12 (0.7) | 10 (6.0) |

$^a$Wells containing resistant cells only

Second Transduction:

A second infection was conducted in both male and female PFF. Transduced cells were plated at densities of 100/well, 200/well, and 500/well on 96-well plates (5 replicates for each density and sex), supplemented with wild type cells to a total of 1,000 cells per well, and selected in G-418 for two weeks. Neomycin resistant colonies appeared in approximately 40, 60, and greater than 90 percent of wells in the 100, 200 and 500 plates respectively (Table 5). Primary PCR screening was performed on the 100 and 200 plates resulting in 13 and 2 positive wells for male and female cells respectively (Table 6). The healthy (11 male and 1 female) colonies were cryopreserved and a portion was set aside for WGA. PCR of both 5' and 3' junctions from WGA DNA revealed positive signal in 8 and 1 of the male and female colonies respectively (FIG. 7 and Table 6). Identity of the junction PCR was confirmed by restriction digest (FIG. 7). Finally, positive clones were analyzed by Southern blotting confirming the knockout allele in each PCR positive clone (FIG. 8).

The presence of the wt allele in male clones 7, 9, 10, 13 indicates a mixed population while the wild type allele in the female clone (Serruys et al., 1994) indicates the knockout is heterozygous.

TABLE 5

96-well plate selection (Second transduction)

| Plating density (cells/well) | Wells | Wells w/ Cells (% wells) | NeoR Colonies (% selected) |
|---|---|---|---|
| 100 Male | 480 | 200 (41) | 200 (0.41) |
| 200 Male | 480 | 279 (58) | 279 (0.29) |
| 100 Female | 480 | 194 (40) | 194 (0.40) |
| 200 Female | 480 | 276 (58) | 276 (0.29) |

TABLE 6

Targeting Frequency (Second transduction)

| | NeoR Colonies (% selected) | 1° PCR Positives (% screened) | 5'-3' PCR RE Positives (% screened) | Frequency (HR positive/selected) |
|---|---|---|---|---|
| Male 20 | 479 (0.33) | 13 (2.27) | 8 (1.67) | $5.5 \times 10^{-5}$ |
| Female 17 | 470 (0.33) | 2 (0.43) | 1 (0.21) | $6.94 \times 10^{-6}$ |

These results show a successful knockout of the dystrophin gene in male and female fibroblasts. These cells are a suitable resource for Somatic cell nuclear transfer and may be used to create founders. The founders and transgenic wine progeny may have a disrupted DMD gene and exhibit a muscular dystrophy phenotype. The DMD gene may be disrupted, for instance, at exon 7, or at other sites that are known to disrupt production of a functional DMD gene product or which have already been established to produce a muscular dystrophy phenotype in other animals. Some or all of the DMD genes may be disrupted. The gene disruption may be performed to prevent expression of a functional Dp427 dystrophin isoform.

A pig model of DMD may be derived from the introduction of mutant alleles most common amongst DMD patients into the pig dystrophin locus by homologous recombination, which are know, e.g., see DYSTROPHIN; DMD-OMIM, which is hereby incorporated herein by reference for all purposes; in case of conflict, the specification is controlling (also Tuffery-Giraud, 2009). Alternatively, ⅓ of the cases of DMD result from a de novo mutation, for which neither parent is a carrier, as is known, see DYSTROPHIN; DMDallelic variants-OMIM, which is hereby incorporated herein by reference for all purposes; in case of conflict, the specification is controlling. Common and de novo alleles could be replicated either by the introduction of previously identified mutant alleles by homologous recombination, gene-conversion, or the introduction of an indel into relevant exons using zinc finger nuclease, meganucleases, TAL effector nucleases, or any other method for targeted DNA breakage/modification. Artisans are able to access gene sequences as may be needed, e.g, DMD cDNA Genebank ID: NM_001012408, Genomic with exon 7 NW_001886608 Exon 2-7 Cross referenced with cDNA, Pig X chromosome NC_010461.2 Cross referenced with cDNA.

Further disclosure relating to DMD genes is provided in U.S. Pat. Nos. 5,239,060, 5,430,129, 5,985,846, 6,653,466, and 7,510,867, which are hereby incorporated by reference herein for all purposes; in case of conflict the instant specification is controlling.

Transgenic Hairless Swine with Disrupted Hairless Gene (HR)

Pig hair is a problematic contaminant for both meat production and derivation of skin derived products. Whereas wild species of swine require hair for protection from the sun, hair is not required for the well-being of modern commercial swine. The hairless (HR) gene encodes a nuclear receptor corepressor that is required for hair growth. Humans and rodents lacking a functional HR gene are born with hair, but are unable to regenerate hair follicles resulting in congenital hair loss early in life (Thompson 2009). Herein, swine cells were made with a disrupted porcine hairless gene (HR) using recombinant Adeno-associated virus (rAAV) homologous recombination. The resultant transfected cells may be used to produce pigs lacking hair by somatic cell nuclear transfer or chromatin transfer.

An rAAV replacement cassette (pAAV-ssHRTGA) was created for targeting of swine HR exon 2 using a fusion PCR technique described in Kohil et al. 2004. Viral packaging was conducted by co-transfection of AAV-293 cells with plasmids: pAAV-ssHRTGA, pAAV-RC, and pAAV-helper. Two days after transfection, cells from one 100 mm plate were lysed in 1 ml of growth media by 3× freeze thaw cycles and stored at −80° C. in 300 microliter aliquots.

Early passage pig fetal fibroblasts were plated at a density of 30,000 cells/cm$^2$ in a single well of a six-well plate to achieve 70-80% confluence within 24 hours. Media was changed 1 hour prior to transduction and replaced with 1 ml of fresh growth medium. One hundred-fifty microliters of viral lysate was added to a single well and incubated under standard growing conditions. After a 24 hour incubation, cells were washed 3× with PBS, trypsinized and plated onto 96 well plates at densities ranging from 125 cells/well to 2,000 cells/well. Plates seeded at low density were adjusted to 1,000 cells per well with wild type fibroblasts to enhance plating efficiency. On the following day, medium containing 300 µg/ml G-418 was added and changed 3× in the course of two weeks. Resistant colonies emerged and were subjected to PCR and Southern analysis. The data indicates a successful knockout of the pig ssHR gene in about 15 cell clones to date.

FIG. 9 depicts the porcine Hairless gene (ssHR) and knockout strategy. Panel (A) depicts the wild type (Wt) ssHR gene, which is comprised of 18 exons, and is located on chromosome 14. The area surrounding exon 2 is highlighted and enlarged. A premature stop codon (TGA) was introduced into exon 2 by rAAV-Homologous recombination to ablate full length ssHR protein in pigs by truncation of the protein. The pAAV-ssHR$^{TGA}$ vector includes the majority of exon 2 and homology arms both up and downstream of exon 2. For selection of targeted cells, two versions of the ssHR$^{TGA}$ were constructed, one with a neomycin (Neo) resistance cassette, another with a puromycin (Puro) resistance cassette. Panel (B) is a schematic that shows the structure of the targeted ssHR$^{TGA}$ allele. The ssHR$^{TGA}$ allele may be used to interfere with full length ssHR production in two ways; by (1) translation terminated at the engineered TGA stop codon and by (2) skipping of exon 3 by alternative splicing between exons 1 and 3 to cause a frame shift mutation.

Embodiments include a swine wherein the disrupted endogenous gene is ssHR. The swine may exhibit a phenotype chosen from the group consisting of hairlessness and reduced hair (one or both). The swine HR gene may be disrupted at ssHR exon 2. The HR gene may also be mutated at other locations as in humans (artisans are able to identify suitable sequences as at, e.g., HAIRLESS, MOUSE, HOMOLOG OF; HR-OMIM, which is hereby incorporated herein by reference for all purposes; in case of conflict, the specification is controlling) by homologous recombination, ZFN, TALENs, to create point mutations, frame shift mutation or early termination resulting in varying levels of severity. Artisans are able to access sequences as needed to establish strategies, and guidance for such strategies has further been set forth herein; see for instance, Genomic sequence Genebank: NC_010456.2, nucleotides 6341979-6360034 Ensembl HR Transcript: NP_001077399.1 (ENSSSCT00000010539).

Further disclosure relating to HR is found in U.S. Publication No. 2005/0176665A1 which is hereby incorporated by reference to the extent it does not contradict what is explicitly disclosed herein.

Swine Cell Transfection

The transfection of swine cells for generation of transgenic animals is customarily a difficult process. As described and demonstrated herein, however, swine cells may be conveniently transfected. A first group of artiodactyl cells may be transfected and then mixed with a second group of artiodactyl cells that have not been so treated. Conventional approaches rely on treating as many cells as possible to enhance the odds that a cell with a desired genetic trait can be found. Counterintuitively, however, it is better to treat fewer cells and hold back untreated cells to mix with them during subsequent culture. Without being bound to a theory of operation, the presence of the untreated cells is believed to produce autocrine and/or paracrine factors that enhance cell survival or cell phenotype, e.g., activation of more preferable DNA repair pathways.

A first embodiment of the method involves introducing an exogenous nucleic acid into a swine cell in vitro comprising exposing a first group of swine cells to a vector that comprises an exogenous nucleic acid during a first culture time period and subsequently adding a second group of swine cells to the first group for a second culture time period, wherein the second group of cells have not been exposed to the vector. The first group and the second group, after being combined, are referred to as a collection, or mixed collection. The mixed collection may be subjected to another round of transfection.

One method involves exposing the first group of cells to transfection agents and then splitting the group into a plurality of cultures. The cultures of the first cell group may be prepared at various seeding densities and allowed to grow for a time period and/or until a desired level of confluence is achieved. A second group of cells may be added to the first group to achieve an overall seeding density and/or after seeding to achieve a desired cell concentration. This second group may be cells that have not been exposed to the transfection agents, and may be wild type cells. The wild type cells may be from the same animal as the first group of cells, or from a different animal of the same or different species. Any of the groups may also be from a pool of animals, for instance a plurality of swine fetuses. The wild type cells may also be from a culture of cells, or a primary or secondary cell culture line. Accordingly, the term wild-type in this specific context of mixing with a group of transfected cells is broad and includes cells transfected by other means. The term native wild-type refers to wild-type cells that have never been modified.

The ratio of wild-type cells to the first group of cells may be, for example, between 0.1:1 and 100:1, or between 0.5:1 and 10:1, or between about 1:1 and about 20:1; artisans will immediately appreciate that all the ranges and values within the explicitly stated ranges are contemplated.

The first group of cells may be seeded at a first seeding density and wild-type cells co-cultured to achieve a total density or confluence. For instance a group of cells may be exposed to transfection agents and then seeded into a plurality of cultures at a seeding density (referring to a concentration per area of cells), e.g., from about 100 to about 10,000 cells per $cm^2$; artisans will immediately appreciate that all the ranges and values within the explicitly stated ranges are contemplated, e.g., about 500 or about 8,000 to about 7,000 or about 10,000. Wild-type cells may then be added to bring the cells to a predetermined concentration, e.g., to a value between 1000 and 100,000 cells/$cm^2$.

The wild-type cells may be added before, during, or after the seeding of the first group of cells. Accordingly, embodiments include seeding the first group of cells and the wild type cells within a 24-hour time period, or at essentially the same time. Embodiments also include seeding the wild-type cells at a time between about 1 day and about 1 week before introduction of the first group of cells exposed to the transfection agents. And embodiments also include seeding the wild-type cells at a time between about 1 day and two weeks after seeding of the first group of cells. Artisans will immediately appreciate that all the ranges and values within the explicitly stated ranges are contemplated.

These methods may be practiced with the various cell types described herein, e.g., fibroblasts, primary fetal swine cells, blastomeres. The cells may be somatic or germ cells. The cells may be an artiodactyl cell, e.g., pig, miniature pig, Ossabow pig. The cells may be adult, juvenile, or fetal, and from any of a variety of tissue sources, e.g., fibroblasts, dermal fibroblasts, dermal, epidermal, mesodermal, mesenchymal, endothelial, vascular, hepatocyte.

These transfection techniques may be used to transfect a cell with an exogenous nucleic acid that disrupts a target gene, e.g., by introduction of a stop codon or by way of other techniques commonly available to an artisan skilled in the art of preventing expression of a nucleic acid in a cell. The genes in the cell may be modified, e.g., LDLR, DMD, and HR.

Cells transfected as described herein may be used to make transgenic artiodactyls (e.g., pigs, sheep, goats, and cows). The nucleated cells of the transgenic artiodactyls contain a nucleic acid construct. As used herein, the term transgenic artiodactyl includes founder transgenic artiodactyls as well as progeny of the founders, progeny of the progeny, and so forth, provided that the progeny retain the nucleic acid construct. For example, a transgenic founder animal can be used to breed additional animals that contain the nucleic acid construct. Transgenic pigs are particularly useful.

Embodiments of the invention include a tissue obtained from the transgenic artiodactyls (e.g., transgenic pigs) and cells derived from the transgenic artiodactyls (e.g., transgenic pigs). As used herein, the term derived from indicates that the cells can be isolated directly from the animal or can be progeny of such cells. For example, an embodiment of the invention is a brain, lung, liver, pancreas, islets, heart and heart valves, muscle, kidney, thyroid, corneal, skin, blood vessel or other connective tissue obtained from a transgenic artiodactyl (e.g., transgenic pig). Blood and hematopoietic cells, Islets of Langerhans, beta cells, brain cells, hepatocytes, kidney cells, and cells from other organs and body fluids, for example, also can be derived from transgenic artiodactyls (e.g., transgenic pigs).

Transgenic Artiodactyls

Various techniques known in the art can be used to introduce nucleic acid constructs into non-human animals to produce founder lines, in which the nucleic acid construct is integrated into the genome. Such techniques include, without limitation, pronuclear microinjection (U.S. Pat. No. 4,873, 191), retrovirus mediated gene transfer into germ lines (Van der Putten et al. (1985) *Proc. Natl. Acad. Sci. USA* 82, 6148-

1652), gene targeting into embryonic stem cells (Thompson et al. (1989) *Cell* 56, 313-321), electroporation of embryos (Lo (1983) *Mol. Cell. Biol.* 3, 1803-1814), sperm mediated gene transfer (Lavitrano et al. (2002) *Proc. Natl. Acad. Sci. USA* 99, 14230-14235; Lavitrano et al. (2006) *Reprod. Fert. Develop.* 18, 19-23), and in vitro transformation of somatic cells, such as cumulus or mammary cells, or adult, fetal, or embryonic stem cells, followed by nuclear transplantation (Wilmut et al. (1997) *Nature* 385, 810-813; and Wakayama et al. (1998) Nature 394, 369-374). Pronuclear microinjection, sperm mediated gene transfer, and somatic cell nuclear transfer are particularly useful techniques.

Typically, in pronuclear microinjection, a nucleic acid construct is introduced into a fertilized egg; 1 or 2 cell fertilized eggs are used as the pronuclei containing the genetic material from the sperm head and the egg are visible within the protoplasm. Pronuclear staged fertilized eggs can be obtained in vitro or in vivo (i.e., surgically recovered from the oviduct of donor animals). In vitro fertilized eggs can be produced as follows. For example, swine ovaries can be collected at an abattoir, and maintained at 22-28° C. during transport. Ovaries can be washed and isolated for follicular aspiration, and follicles ranging from 4-8 mm can be aspirated into 50 mL conical centrifuge tubes using 18 gauge needles and under vacuum. Follicular fluid and aspirated oocytes can be rinsed through pre-filters with commercial TL-HEPES (Minitube, Verona, Wis.). Oocytes surrounded by a compact cumulus mass can be selected and placed into TCM-199 OOCYTE MATURATION MEDIUM (Minitube, Verona, Wis.) supplemented with 0.1 mg/mL cysteine, 10 ng/mL epidermal growth factor, 10% porcine follicular fluid, 50 µM 2-mercaptoethanol, 0.5 mg/ml cAMP, 10 IU/mL each of pregnant mare serum gonadotropin (PMSG) and human chorionic gonadotropin (hCG) for approximately 22 hours in humidified air at 38.7° C. and 5% $CO_2$. Subsequently, the oocytes can be moved to fresh TCM-199 maturation medium which will not contain cAMP, PMSG or hCG and incubated for an additional 22 hours. Matured oocytes can be stripped of their cumulus cells by vortexing in 0.1% hyaluronidase for 1 minute.

Mature oocytes can be fertilized in 500 µl Minitube PORCPRO IVF MEDIUM SYSTEM (Minitube, Verona, Wis.) in Minitube 5-well fertilization dishes. In preparation for in vitro fertilization (IVF), freshly-collected or frozen boar semen can be washed and resuspended in PORCPRO IVF Medium to $4 \times 10^5$ sperm. Sperm concentrations can be analyzed by computer assisted semen analysis (SPERMVISION, Minitube, Verona, Wis.). Final in vitro insemination can be performed in a 10 µl volume at a final concentration of approximately 40 motile sperm/oocyte, depending on boar. Incubate all fertilizing oocytes at 38.7° C. in 5.0% $CO_2$ atmosphere for 6 hours. Six hours post-insemination, presumptive zygotes can be washed twice in NCSU-23 and moved to 0.5 mL of the same medium. This system can produce 20-30% blastocysts routinely across most boars with a 10-30% polyspermic insemination rate.

Linearized nucleic acid constructs can be injected into one of the pronuclei then the injected eggs can be transferred to a recipient female (e.g., into the oviducts of a recipient female) and allowed to develop in the recipient female to produce the transgenic animals. In particular, in vitro fertilized embryos can be centrifuged at 15,000×g for 5 minutes to sediment lipids allowing visualization of the pronucleus. The embryos can be injected with approximately 5 picoliters of the transposon/transposase cocktail using an Eppendorf FEMTOJET injector and can be cultured until blastocyst formation (~144 hours) in NCSU 23 medium (see, e.g., PCT Publication No. 2006/036975). Rates of embryo cleavage and blastocyst formation and quality can be recorded.

Embryos can be surgically transferred into uteri of asynchronous recipients. For surgical embryo transfer, anesthesia can be induced with a combination of the following: ketamine (2 mg/kg); tiletamine/zolazepam (0.25 mg/kg); xylazine (1 mg/kg); and atropine (0.03 mg/kg) (all from Columbus Serum). While in dorsal recumbency, the recipients can be aseptically prepared for surgery and a caudal ventral incision can be made to expose and examine the reproductive tract. Typically, 100-200 (e.g., 150-200) embryos can be deposited into the ampulla-isthmus junction of the oviduct using a 5.5-inch TOMCAT® catheter. After surgery, real-time ultrasound examination of pregnancy can be performed using an ALOKA 900 ultrasound scanner (Aloka Co. Ltd, Wallingford, Conn.) with an attached 3.5 MHz trans-abdominal probe. Monitoring for pregnancy initiation can begin at 23 days post fusion and can be repeated weekly during pregnancy. Recipient husbandry can be maintained as normal gestating sows.

In somatic cell nuclear transfer, a transgenic artiodactyl cell (e.g., a transgenic pig cell) such as an embryonic blastomere, fetal fibroblast, adult ear fibroblast, or granulosa cell that includes a nucleic acid construct described above, can be introduced into an enucleated oocyte to establish a combined cell. Oocytes can be enucleated by partial zona dissection near the polar body and then pressing out cytoplasm at the dissection area. Typically, an injection pipette with a sharp beveled tip is used to inject the transgenic cell into an enucleated oocyte arrested at meiosis 2. In some conventions, oocytes arrested at meiosis 2 are termed "eggs." After producing a porcine embryo (e.g., by fusing and activating the oocyte), the porcine embryo is transferred to the oviducts of a recipient female, about 20 to 24 hours after activation. See, for example, Cibelli et al. (1998) *Science* 280, 1256-1258 and U.S. Pat. No. 6,548,741. For pigs, recipient females can be checked for pregnancy approximately 20-21 days after transfer of the embryos.

Standard breeding techniques can be used to create animals that are homozygous for the target nucleic acid from the initial heterozygous founder animals. Homozygosity may not be required, however. Transgenic pigs described herein can be bred with other pigs of interest.

In some embodiments, a nucleic acid of interest and a selectable marker can be provided on separate transposons and provided to either embryos or cells in unequal amount, where the amount of transposon containing the selectable marker far exceeds (5-10 fold excess) the transposon containing the nucleic acid of interest. Transgenic cells or animals expressing the nucleic acid of interest can be isolated based on presence and expression of the selectable marker. Because the transposons will integrate into the genome in a precise and unlinked way (independent transposition events), the nucleic acid of interest and the selectable marker are not genetically linked and can easily be separated by genetic segregation through standard breeding. Thus, transgenic animals can be produced that are not constrained to retain selectable markers in subsequent generations, an issue of some concern from a public safety perspective.

Once transgenic animal have been generated, expression of a target nucleic acid can be assessed using standard techniques. Initial screening can be accomplished by Southern blot analysis to determine whether or not integration of the construct has taken place. For a description of Southern analysis, see sections 9.37-9.52 of Sambrook et al., 1989, *Molecular Cloning, A Laboratory Manual*, second edition, Cold Spring Harbor Press, Plainview; NY. Polymerase chain reaction (PCR) techniques also can be used in the initial screening PCR refers to a procedure or technique in which target nucleic acids are amplified. Generally, sequence information from the ends of the region of interest or beyond is employed to design oligonucleotide primers that are identical or similar in sequence to opposite strands of the template to be amplified. PCR can be used to amplify specific sequences from DNA as well as RNA, including sequences from total genomic DNA or total cellular RNA. Primers typically are 14 to 40 nucleotides in length, but can range from 10 nucleotides to hundreds of nucleotides in length. PCR is described in, for example *PCR Primer: A Laboratory Manual*, ed. Dieffenbach and Dveksler, Cold Spring Harbor Laboratory Press, 1995. Nucleic acids also can be amplified by ligase chain reaction, strand displacement amplification, self-sustained sequence replication, or nucleic acid sequence-based amplified. See, for example, Lewis (1992) *Genetic Engineering News* 12, 1; Guatelli et al. (1990) *Proc. Natl. Acad. Sci. USA* 87, 1874-1878; and Weiss (1991) *Science* 254, 1292-1293. At the blastocyst stage, embryos can be individually processed for analysis by PCR, Southern hybridization and splinkerette PCR (see, e.g., Dupuy et al. *Proc Natl Acad Sci USA* (2002) 99(7):4495-4499).

Expression of a nucleic acid sequence encoding a polypeptide in the tissues of transgenic pigs can be assessed using techniques that include, for example, Northern blot analysis of tissue samples obtained from the animal, in situ hybridization analysis, Western analysis, immunoassays such as enzyme-linked immunosorbent assays, and reverse-transcriptase PCR (RT-PCR).

Vectors and Nucleic Acids

A variety of nucleic acids may be introduced into the swine cells, for knockout purposes, or to obtain expression of a gene for other purposes. Nucleic acid constructs that can be used to produce transgenic animals include a target nucleic acid sequence. As used herein, the term nucleic acid includes DNA, RNA, and nucleic acid analogs, and nucleic acids that are double-stranded or single-stranded (i.e., a sense or an antisense single strand). Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-doxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six membered, morpholino ring, or peptide nucleic acids, in which the deoxyphosphate backbone is replaced by a pseudopeptide backbone and the four bases are retained. See, Summerton and Weller (1997) *Antisense Nucleic Acid Drug Dev.* 7(3):187-195; and Hyrup et al. (1996) *Bioorgan. Med. Chem.* 4(1):5-23. In addition, the deoxyphosphate backbone can be replaced with, for example, a phosphorothioate or phosphorodithioate backbone, a phosphoroamidite, or an alkyl phosphotriester backbone.

The target nucleic acid sequence can be operably linked to a regulatory region such as a promoter. Regulatory regions can be porcine regulatory regions or can be from other species. As used herein, operably linked refers to positioning of a regulatory region relative to a nucleic acid sequence in such a way as to permit or facilitate transcription of the target nucleic acid.

Any type of promoter can be operably linked to a target nucleic acid sequence. Examples of promoters include, without limitation, tissue-specific promoters, constitutive promoters, and promoters responsive or unresponsive to a particular stimulus. Suitable tissue specific promoters can result in preferential expression of a nucleic acid transcript in θ cells and include, for example, the human insulin promoter. Other tissue specific promoters can result in preferential expression in, for example, hepatocytes or heart tissue and can include the albumin or alpha-myosin heavy chain promoters, respectively. In other embodiments, a promoter that facilitates the expression of a nucleic acid molecule without significant tissue- or temporal-specificity can be used (i.e., a constitutive promoter). For example, a beta-actin promoter such as the chicken θ-actin gene promoter, ubiquitin promoter, miniCAGs promoter, glyceraldehyde-3-phosphate dehydrogenase (GAPDH) promoter, or 3-phosphoglycerate kinase (PGK) promoter can be used, as well as viral promoters such as the herpes virus thymidine kinase (TK) promoter, the SV40 promoter, or a cytomegalovirus (CMV) promoter. In some embodiments, a fusion of the chicken θ actin gene promoter and the CMV enhancer is used as a promoter. See, for example, Xu et al. (2001) *Hum. Gene Ther.* 12(5):563-73; and Kiwaki et al. (1996) *Hum. Gene Ther.* 7(7):821-30.

An example of an inducible promoter is the tetracycline (tet)-on promoter system, which can be used to regulate transcription of the nucleic acid. In this system, a mutated Tet repressor (TetR) is fused to the activation domain of herpes simplex VP 16 (transactivator protein) to create a tetracycline-controlled transcriptional activator (tTA), which is regulated by tet or doxycycline (dox). In the absence of antibiotic, transcription is minimal, while in the presence of tet or dox, transcription is induced. Alternative inducible systems include the ecdysone or rapamycin systems. Ecdysone is an insect molting hormone whose production is controlled by a heterodimer of the ecdysone receptor and the product of the ultraspiracle gene (USP). Expression is induced by treatment with ecdysone or an analog of ecdysone such as muristerone A. The agent that is administered to the animal to trigger the inducible system is referred to as an induction agent.

Additional regulatory regions that may be useful in nucleic acid constructs, include, but are not limited to, polyadenylation sequences, translation control sequences (e.g., an internal ribosome entry segment, IRES), enhancers, inducible elements, or introns. Such regulatory regions may not be necessary, although they may increase expression by affecting transcription, stability of the mRNA, translational efficiency, or the like. Such regulatory regions can be included in a nucleic acid construct as desired to obtain optimal expression of the nucleic acids in the cell(s). Sufficient expression, however, can sometimes be obtained without such additional elements.

Other elements that can be included on a nucleic acid construct encode signal peptides or selectable markers. Signal peptides can be used such that an encoded polypeptide is directed to a particular cellular location (e.g., the cell surface). Non-limiting examples of selectable markers include puromycin, adenosine deaminase (ADA), aminoglycoside phosphotransferase (neo, G418, APH), dihydrofolate reductase (DHFR), hygromycin-B-phosphtransferase, thymidine kinase (TK), and xanthin-guanine phosphoribosyltransferase (XGPRT). Such markers are useful for selecting stable transformants in culture. Other selectable markers include fluorescent polypeptides, such as green fluorescent protein or yellow fluorescent protein.

In some embodiments, a sequence encoding a selectable marker can be flanked by recognition sequences for a recombinase such as, e.g., Cre or Flp. For example, the selectable marker can be flanked by loxP recognition sites (34 bp recognition sites recognized by the Cre recombinase) or FRT recognition sites such that the selectable marker can be excised from the construct. See, Orban, et al., *Proc. Natl. Acad. Sci.* (1992) 89 (15): 6861-6865, for a review of Cre/lox technology, and Branda and Dymecki, *Dev. Cell* (2004) 6(1): 7-28. A transposon containing a Cre- or Flp-activatable transgene interrupted by a selectable marker gene also can be used to obtain transgenic animals with conditional expression of a transgene. For example, a promoter driving expression of the marker/transgene can be either ubiquitous or tissue-specific, which would result in the ubiquitous or tissue-specific expression of the marker in F0 animals (e.g., pigs). Tissue specific activation of the transgene can be accomplished, for example, by crossing a pig that ubiquitously expresses a marker-interrupted transgene to a pig expressing Cre or Flp in a tissue-specific manner, or by crossing a pig that expresses a marker-interrupted transgene in a tissue-specific manner to a pig that ubiquitously expresses Cre or Flp recombinase. Controlled expression of the transgene or controlled excision of the marker allows expression of the transgene.

In some embodiments, the target nucleic acid encodes a polypeptide. A nucleic acid sequence encoding a polypeptide can include a tag sequence that encodes a "tag" designed to facilitate subsequent manipulation of the encoded polypeptide (e.g., to facilitate localization or detection). Tag sequences can be inserted in the nucleic acid sequence encoding the polypeptide such that the encoded tag is located at either the carboxyl or amino terminus of the polypeptide. Non-limiting examples of encoded tags include glutathione S-transferase (GST) and FLAG™ tag (Kodak, New Haven, Conn.).

In other embodiments, the target nucleic acid sequence induces RNA interference against a target nucleic acid such that expression of the target nucleic acid is reduced. For example the target nucleic acid sequence can induce RNA interference against a nucleic acid encoding a cystic fibrosis transmembrane conductance regulatory (CFTR) polypeptide. For example, double-stranded small interfering RNA (siRNA) or small hairpin RNA (shRNA) homologous to a CFTR DNA can be used to reduce expression of that DNA. Constructs for siRNA can be produced as described, for example, in Fire et al. (1998) *Nature* 391:806-811; Romano and Macino (1992) *Mol. Microbiol.* 6:3343-3353; Cogoni et al. (1996) *EMBO J.* 15:3153-3163; Cogoni and Macino (1999) *Nature* 399:166-169; Misquitta and Paterson (1999) *Proc. Natl. Acad. Sci. USA* 96:1451-1456; and Kennerdell and Carthew (1998) *Cell* 95:1017-1026. Constructs for shRNA can be produced as described by McIntyre and Fanning (2006) *BMC Biotechnology* 6:1. In general, shRNAs are transcribed as a single-stranded RNA molecule containing complementary regions, which can anneal and form short hairpins.

Nucleic acid constructs can be methylated using an SssI CpG methylase (New England Biolabs, Ipswich, Mass.). In general, the nucleic acid construct can be incubated with S-adenosylmethionine and SssI CpG-methylase in buffer at 37° C. Hypermethylation can be confirmed by incubating the construct with one unit of HinP1I endonuclease for 1 hour at 37° C. and assaying by agarose gel electrophoresis.

Nucleic acid constructs can be introduced into embryonic, fetal, or adult porcine cells of any type, including, for example, germ cells such as an oocyte or an egg, a progenitor cell, an adult or embryonic stem cell, a kidney cell such as a PK-15 cell, an islet cell, a beta cell, a liver cell, or a fibroblast such as a dermal fibroblast, using a variety of techniques. Non-limiting examples of techniques include the use of transposon systems, recombinant viruses that can infect cells, or liposomes or other non-viral methods such as electroporation, microinjection, or calcium phosphate precipitation, that are capable of delivering nucleic acids to cells.

In transposon systems, the transcriptional unit of a nucleic acid construct, i.e., the regulatory region operably linked to a target nucleic acid sequence, is flanked by an inverted repeat of a transposon. Several transposon systems, including, for example, Sleeping Beauty (see, U.S. Pat. No. 6,613,752 and U.S. Publication No. 2005/0003542); Frog Prince (Miskey et al. (2003) *Nucleic Acids Res.* 31(23):6873-81); Tol2 (Kawakami (2007) *Genome Biology* 8(Suppl. 1):S7; Minos (Pavlopoulos et al. (2007) *Genome Biology* 8(Suppl. 1):S2); Hsma1 (Miskey et al. (2007)) *Mol Cell Biol.* 27(12):4589-600); and Passport (Leaver (2001) *Gene,* 271(2), 203-214) have been developed to introduce nucleic acids into cells, including mice, human, and pig cells. The Sleeping Beauty transposon is particularly useful. A transposase can be encoded on the same nucleic acid construct as the target nucleic acid, can be introduced on a separate nucleic acid construct, or provided as an mRNA (e.g., an in vitro transcribed and capped mRNA).

Insulator elements also can be included in a nucleic acid construct to maintain expression of the target nucleic acid and to inhibit the unwanted transcription of host genes. See, for example, U.S. Publication No. 2004/0203158. Typically, an insulator element flanks each side of the transcriptional unit and is internal to the inverted repeat of the transposon. Non-limiting examples of insulator elements include the matrix attachment region (MAR) type insulator elements and border-type insulator elements. See, for example, U.S. Pat. Nos. 6,395,549, 5,731,178, 6,100,448, and 5,610,053, and U.S. Publication No. 2004/0203158.

Nucleic acids can be incorporated into vectors. A vector is a broad term that includes any specific DNA segment that is designed to move from a carrier into a target DNA. A vector may be referred to as an expression vector, or a vector system, which is a set of components needed to bring about DNA insertion into a genome or other targeted DNA sequence such as an episome, plasmid, or even virus/phage DNA segment. Vector systems such as viral vectors (e.g., retroviruses, adeno-associated virus and integrating phage viruses), and non-viral vectors (e.g., transposons) used for gene delivery in animals have two basic components: 1) a vector comprised of DNA (or RNA that is reverse transcribed into a cDNA) and 2) a transposase, recombinase, or other integrase enzyme that recognizes both the vector and a DNA target sequence and inserts the vector into the target DNA sequence. Vectors most often contain one or more expression cassettes that comprise one or more expression control sequences, wherein an expression control sequence is a DNA sequence that controls and regulates the transcription and/or translation of another DNA sequence or mRNA, respectively.

Many different types of vectors are known. For example, plasmids and viral vectors, e.g., retroviral vectors, are known. Mammalian expression plasmids typically have an origin of replication, a suitable promoter and optional enhancer, and also any necessary ribosome binding sites, a polyadenylation site, splice donor and acceptor sites, transcriptional termination sequences, and 5' flanking non-transcribed sequences. Examples of vectors include: plasmids (which may also be a carrier of another type of vector), adenovirus, adeno-associated virus (AAV), lentivirus (e.g., modified HIV-1, SIV or FIV), retrovirus (e.g., ASV, ALV or MoMLV), and transposons (e.g., Sleeping Beauty, P-elements, Tol-2, Frog Prince, piggyBac).

As used herein, the term nucleic acid refers to both RNA and DNA, including, for example, cDNA, genomic DNA, synthetic (e.g., chemically synthesized) DNA, as well as naturally occurring and chemically modified nucleic acids, e.g., synthetic bases or alternative backbones. A nucleic acid molecule can be double-stranded or single-stranded (i.e., a sense or an antisense single strand). The term transgenic is used broadly herein and refers to a genetically modified organism or genetically engineered organism whose genetic material has been altered using genetic engineering techniques. A knockout artiodactyl is thus transgenic regardless of whether or not exogenous genes or nucleic acids are expressed in the animal or its progeny.

The publications, patents, and patent applications referenced in this document are hereby incorporated by reference herein in their entirety for all purposes; in case of conflict, the specification controls. Headings in this document are provided for reference and are not limiting with respect to the scope of the embodiments of the invention.

REFERENCES

Daugherty A. Mouse models of atherosclerosis. *Am J Med Sci* 2002; 323(1):3-10.

Rapacz J, Hasler-Rapacz J, Taylor K M, Checovich W J, Attie A D. Lipoprotein mutations in pigs are associated with elevated plasma cholesterol and atherosclerosis. *Science* 1986; 234(4783):1573-7.

Hasler-Rapacz J, Ellegren H, Fridolfsson A K, et al. Identification of a mutation in the low density lipoprotein receptor gene associated with recessive familial hypercholesterolemia in swine. *Am J Med Genet* 1998; 76(5):379-86.

Prescott M F, McBride C H, Hasler-Rapacz J, Von Linden J, Rapacz J. Development of complex atherosclerotic lesions in pigs with inherited hyper-LDL cholesterolemia bearing mutant alleles for apolipoprotein B. *Am J Pathol* 1991; 139(1):139-47.

Lee D M, Mok T, Hasler-Rapacz J, Rapacz J. Concentrations and compositions of plasma lipoprotein subfractions of Lpb5-Lpu1 homozygous and heterozygous swine with hypercholesterolemia. *J Lipid Res* 1990; 31 (5): 839-47.

Lowe S W, Checovich W J, Rapacz J, Attie A D. Defective receptor binding of low density lipoprotein from pigs possessing mutant apolipoprotein B alleles. *J Biol Chem* 1988; 263(30): 15467-73.

Grunwald K A, Schueler K, Uelmen P J, et al. Identification of a novel Arg→Cys mutation in the LDL receptor that contributes to spontaneous hypercholesterolemia in pigs. *J Lipid Res* 1999; 40(3):475-85.

Aiello R J, Nevin D N, Ebert D L, et al. Apolipoprotein B and a second major gene locus contribute to phenotypic variation of spontaneous hypercholesterolemia in pigs. *Arterioscler Thromb* 1994; 14(3):409-19.

Hirata R, Chamberlain J, Dong R, Russell D W. Targeted transgene insertion into human chromosomes by adeno-associated virus vectors. *Nat Biotechnol* 2002; 20(7):735-8.

Hirata R K, Xu C, Dong R, Miller D G, Ferguson S, Russell D W. Efficient PRNP gene targeting in bovine fibroblasts by adeno-associated virus vectors. *Cloning Stem Cells* 2004; 6(1):31-6.

Fattori R, Piva T. Drug-eluting stents in vascular intervention. *Lancet* 2003; 361(9353):247-9.

Holmes D R, Jr., Savage M, LaBlanche J M, et al. Results of Prevention of REStenosis with Tranilast and its Outcomes (PRESTO) trial. *Circulation* 2002; 106(10):1243-50.

Investigators T E. Acute platelet inhibition with abciximab does not reduce in-stent restenosis (ERASER study). The ERASER Investigators. *Circulation* 1999; 100(8):799-806.

vom Dahl J, Dietz U, Haager P K, et al. Rotational atherectomy does not reduce recurrent in-stent restenosis: results of the angioplasty versus rotational atherectomy for treatment of diffuse in-stent restenosis trial (ARTIST). *Circulation* 2002; 105(5):583-8.

Topol E J, Mark D B, Lincoff A M, et al. Outcomes at 1 year and economic implications of platelet glycoprotein IIb/IIIa blockade in patients undergoing coronary stenting: results from a multicentre randomised trial. EPISTENT Investigators. Evaluation of Platelet IIb/IIIa Inhibitor for Stenting. *Lancet* 1999; 354(9195):2019-24.

Serruys P W, Kay I P, Disco C, Deshpande N V, de Feyter P J. Periprocedural quantitative coronary angiography after Palmaz-Schatz stent implantation predicts the restenosis rate at six months: results of a meta-analysis of the BElgian NEtherlands Stent study (BENESTENT) I, BENESTENT II Pilot, BENESTENT II and MUSIC trials. Multicenter Ultrasound Stent In Coronaries. *J Am Coll Cardiol* 1999; 34(4):1067-74.

Serruys P W, de Jaegere P, Kiemeneij F, et al. A comparison of balloon-expandable-stent implantation with balloon angioplasty in patients with coronary artery disease. Benestent Study Group. *N Engl J Med* 1994; 331(8):489-95.

Moer R, Myreng Y, Molstad P, et al. Stenting in small coronary arteries (SISCA) trial. A randomized comparison between balloon angioplasty and the heparin-coated beStent. *J Am Coll Cardiol* 2001; 38(6):1598-603.

Muni N I, Gross T P. Problems with drug-eluting coronary stents—the FDA perspective. *N Engl J Med* 2004; 351(16): 1593-5.

Lafont A. The Cypher stent: no longer efficacious at three months in the porcine model? *Cardiovasc Res* 2004; 63(4): 575-6.

McFadden E P, Stabile E, Regar E, et al. Late thrombosis in drug-eluting coronary stents after discontinuation of antiplatelet therapy. *Lancet* 2004; 364(9444):1519-21.

Tumbleson M E, Schook L B. Advances in swine in biomedical research. New York: Plenum Press, 1996.

Mahley R W, Weisgraber K H. An electrophoretic method for the quantitative isolation of human and swine plasma lipoproteins. *Biochemistry* 1974; 13(9):1964-9.

Ruof J, Klein G, Marz W, Wollschlager H, Neiss A, Wehling M. Lipid-lowering medication for secondary prevention of coronary heart disease in a German outpatient population: the gap between treatment guidelines and real life treatment patterns. *Prev Med* 2002; 35(1):48-53.

Marz W, Wollschlager H, Klein G, Neiss A, Wehling M. Safety of low-density lipoprotein cholestrol reduction with atorvastatin versus simvastatin in a coronary heart disease population (the TARGET TANGIBLE trial). *Am J Cardiol* 1999; 84(1):7-13.

Kuivenhoven J A, Jukema J W, Zwinderman A H, et al. The role of a common variant of the cholesteryl ester transfer protein gene in the progression of coronary atherosclerosis. The Regression Growth Evaluation Statin Study Group. *N Engl J Med* 1998; 338(2):86-93.

McPherson R, Hanna K, Agro A, Braeken A. Cerivastatin versus branded pravastatin in the treatment of primary hypercholesterolemia in primary care practice in Canada: a one-year, open-label, randomized, comparative study of efficacy, safety, and cost-effectiveness. *Clin Ther* 2001; 23(9): 1492-507.

Henwood J M, Heel R C. Lovastatin. A preliminary review of its pharmacodynamic properties and therapeutic use in hyperlipidaemia. *Drugs* 1988; 36(4):429-54.

Harris A. Towards an ovine model of cystic fibrosis. *Hum Mol Genet* 1997; 6(13):2191-4.

Coleman R A. Of mouse and man—what is the value of the mouse in predicting gene expression in humans? *Drug Discov Today* 2003; 8(6):233-5.

Marx J. Medicine. Building better mouse models for studying cancer. *Science* 2003; 299(5615):1972-5.

Harm B, Balmain A. Building 'validated' mouse models of human cancer. *Curr Opin Cell Biol* 2001; 13(6): 778-84.

Janus C, Westaway D. Transgenic mouse models of Alzheimer's disease. *Physiol Behav* 2001; 73(5):873-86.

Lo D. Animal models of human disease. Transgenic and knockout models of autoimmunity: Building a better disease? *Clin Immunol Immunopathol* 1996; 79(2):96-104.

Mehihop P D, van de Rijn M, Goldberg A B, et al. Allergen-induced bronchial hyperreactivity and eosinophilic inflammation occur in the absence of IgE in a mouse model of asthma. *Proc Natl Acad Sci USA* 1997; 94(4): 1344-9.

Grisham J W. Interspecies comparison of liver carcinogenesis: implications for cancer risk assessment. *Carcinogenesis* 1997; 18(1):59-81.

Piedrahita J A. Targeted modification of the domestic animal genome. *Theriogenology* 2000; 53(1):105-16.

Polejaeva I A. Cloning pigs: advances and applications. *Reprod Suppl* 2001; 58:293-300.

Wheeler M B, Walters E M. Transgenic technology and applications in swine. *Theriogenology* 2001; 56(8):1345-69.

Charreau B, Tesson L, Soulillou J P, Pourcel C, Anegon I. Transgenesis in rats: technical aspects and models. *Transgenic Res* 1996; 5(4):223-34.

Kuroiwa Y, Kasinathan P, Matsushita H, et al. Sequential targeting of the genes encoding immunoglobulin-mu and prion protein in cattle. *Nat Genet* 2004; 36(7):775-80.

Kolber-Simonds D, Lai L, Watt S R, et al. Production of alpha-1,3-galactosyltransferase null pigs by means of nuclear transfer with fibroblasts bearing loss of heterozygosity mutations. *Proc Natl Acad Sci USA* 2004; 101(19): 7335-40.

Glass C K, Witztum J L. Atherosclerosis. the road ahead. *Cell* 2001; 104(4):503-16.

Bernstein D. Exercise assessment of transgenic models of human cardiovascular disease. *Physiol Genomics* 2003; 13(3): 217-26.

Guidance for the Submission of Research and Marketing Application for Interventional Cardiology Devices: PTCA Catheters, Atherectomy Catheters, Lasers, Intravascular Stents. Food and Drug Administration, Center for Devices and Radiological Health, U.S. Dept. Health and Human Service, 1995.

Veniant M M, Withycombe S, Young S G. Lipoprotein size and atherosclerosis susceptibility in Apoe(−/−) and Ldlr (−/−) mice. *Arterioscler Thromb Vase Biol* 2001; 21(10): 1567-70.

Badimon L, Chesebro J H, Badimon J J. Thrombus formation on ruptured atherosclerotic plaques and rethrombosis on evolving thrombi. *Circulation* 1992; 86(6 Suppl):11174-85.

Grainger D J, Reckless J, McKilligin E. Apolipoprotein E modulates clearance of apoptotic bodies in vitro and in vivo, resulting in a systemic proinflammatory state in apolipoprotein E-deficient mice. *J Immunol* 2004; 173 (10): 6366-75.

Kohila, T., E. Parkkonen, et al. (2004). "Evaluation of the effects of aluminium, ethanol and their combination on rat brain synaptosomal integral proteins in vitro and after 90-day oral exposure." *Arch Toxicol* 78(5): 276-282.

Thompson, C. C. (2009). "Hairless is a nuclear receptor corepressor essential for skin function." *Nucl Recept Signal* 7: e010.

Rapacz J, Hasler-Rapacz J. Animal Models: The Pig. In: Sparkes R S, Lusis A J, eds. Genetic factors in atherosclerosis: approaches and model systems. Basel; New York: Karger, 1989: 139-169.

Koenig, M., Monaco, A. P. and Kunkel, L. M. (1988) The complete sequence of dystrophin predicts a rod-shaped cytoskeletal protein. *Cell,* 53, 219-228.

Yoshida, M. and Ozawa, E. (1990) Glycoprotein complex anchoring dystrophin to sarcolemma. *Journal of biochemistry,* 108, 748-752.

Ervasti, J. M., Ohlendieck, K., Kahl, S. D., Gaver, M. G. and Campbell, K. P. (1990) Deficiency of a glycoprotein component of the dystrophin complex in dystrophic muscle. *Nature,* 345, 315-319.

Suzuki, A., Yoshida, M., Yamamoto, H. and Ozawa, E. (1992) Glycoprotein-binding site of dystrophin is confined to the cysteine-rich domain and the first half of the carboxy-terminal domain. *FEBS letters,* 308, 154-160.

Jung, D., Yang, B., Meyer, J., Chamberlain, J. S, and Campbell, K. P. (1995) Identification and characterization of the dystrophin anchoring site on beta-dystroglycan. *The Journal of biological chemistry,* 270, 27305-27310.

Ahn, A. H. and Kunkel, L. M. (1993) The structural and functional diversity of dystrophin. *Nature genetics,* 3, 283-291.

Campbell, K. P. (1995) Three muscular dystrophies: loss of cytoskeleton-extracellular matrix linkage. *Cell,* 80, 675-679.

Ozawa, E., Yoshida, M., Suzuki, A., Mizuno, Y., Hagiwara, Y. and Noguchi, S. (1995) Dystrophin-associated proteins in muscular dystrophy. *Hum Mol Genet,* 4 Spec No, 1711-1716.

Nudel, U., Zuk, D., Einat, P., Zeelon, E., Levy, Z., Neuman, S, and Yaffe, D. (1989) Duchenne muscular dystrophy gene product is not identical in muscle and brain. *Nature,* 337, 76-78.

Barnea, E., Zuk, D., Simantov, R., Nudel, U. and Yaffe, D. (1990) Specificity of expression of the muscle and brain dystrophin gene promoters in muscle and brain cells. *Neuron,* 5, 881-888.

Boyce, F. M., Beggs, A. H., Feener, C. and Kunkel, L. M. (1991) Dystrophin is transcribed in brain from a distant upstream promoter. *Proc Natl Acad Sci USA,* 88, 1276-1280.

Gorecki, D. C., Monaco, A. P., Derry, J. M., Walker, A. P., Barnard, E. A. and Barnard, P. J. (1992) Expression of four alternative dystrophin transcripts in brain regions regulated by different promoters. *Hum Mol Genet,* 1, 505-510.

Bar, S., Barnea, E., Levy, Z., Neuman, S., Yaffe, D. and Nudel, U. (1990) A novel product of the Duchenne muscular dystrophy gene which greatly differs from the known isoforms in its structure and tissue distribution. *The Biochemical journal,* 272, 557-560.

Lederfein, D., Levy, Z., Augier, N., Mornet, D., Morris, G., Fuchs, O., Yaffe, D. and Nudel, U. (1992) A 71-kilodalton protein is a major product of the Duchenne muscular dystrophy gene in brain and other nonmuscle tissues. *Proc Natl Acad Sci USA,* 89, 5346-5350.

Rapaport, D., Lederfein, D., den Dunnen, J. T., Grootscholten, P. M., Van Ommen, G. J., Fuchs, O., Nudel, U. and Yaffe, D. (1992) Characterization and cell type distribution of a novel, major transcript of the Duchenne muscular dystrophy gene. *Differentiation; research in biological diversity,* 49, 187-193.

Greenberg, D. S., Schatz, Y., Levy, Z., Pizzo, P., Yaffe, D. and Nudel, U. (1996) Reduced levels of dystrophin associated proteins in the brains of mice deficient for Dp71. *Hum Mol Genet*, 5, 1299-1303.

Byers, T. J., Lidov, H. G. and Kunkel, L. M. (1993) An alternative dystrophin transcript specific to peripheral nerve. *Nature genetics*, 4, 77-81.

Lidov, H. G., Selig, S, and Kunkel, L. M. (1995) Dp140: a novel 140 kDa CNS transcript from the dystrophin locus. *Hum Mol Genet*, 4, 329-335.

D'Souza, V. N., Nguyen, T. M., Morris, G. E., Karges, W., Pillers, D. A. and Ray, P. N. (1995) A novel dystrophin isoform is required for normal retinal electrophysiology. *Hum Mol Genet*, 4, 837-842.

Cox, G. A., Sunada, Y., Campbell, K. P. and Chamberlain, J. S. (1994) Dp71 can restore the dystrophin-associated glycoprotein complex in muscle but fails to prevent dystrophy. *Nature genetics*, 8, 333-339.

Greenberg, D. S., Sunada, Y., Campbell, K. P., Yaffe, D. and Nudel, U. (1994) Exogenous Dp71 restores the levels of dystrophin associated proteins but does not alleviate muscle damage in mdx mice. *Nature genetics*, 8, 340-344.

Leibovitz, S., Meshorer, A., Fridman, Y., Wieneke, S., Jockusch, H., Yaffe, D. and Nudel, U. (2002) Exogenous Dp71 is a dominant negative competitor of dystrophin in skeletal muscle. *Neuromuscul Disord*, 12, 836-844.

Bell, C. D. and Conen, P. E. (1968) Histopathological changes in Duchenne muscular dystrophy. *J Neurol Sci*, 7, 529-544.

Hasegawa, T., Matsumura, K., Hashimoto, T., Ikehira, H., Fukuda, H. and Tateno, Y. (1992) [Intramuscular degeneration process in Duchenne muscular dystrophy—investigation by longitudinal MR imaging of the skeletal muscles]. *Rinsho Shinkeigaku*, 32, 333-335.

Nagao, H., Morimoto, T., Sano, N., Takahashi, M., Nagai, H., Tawa, R., Yoshimatsu, M., Woo, Y. J. and Matsuda, H. (1991) [Magnetic resonance imaging of skeletal muscle in patients with Duchenne muscular dystrophy—serial axial and sagittal section studies]. *No To Hattatsu*, 23, 39-43.

Law, D. J. and Tidball, J. G. (1993) Dystrophin deficiency is associated with myotendinous junction defects in prenecrotic and fully regenerated skeletal muscle. *Am J Pathol*, 142, 1513-1523.

Banks, G. B., Choy, P. T., Lavidis, N. A. and Noakes, P. G. (2003) Neuromuscular synapses mediate motor axon branching and motoneuron survival during the embryonic period of programmed cell death. *Developmental biology*, 257, 71-84.

Carlson, C. G. and Roshek, D. M. (2001) Adult dystrophic (mdx) endplates exhibit reduced quantal size and enhanced quantal variation. *Pflugers Arch*, 442, 369-375.

Lyons, P. R. and Slater, C. R. (1991) Structure and function of the neuromuscular junction in young adult mdx mice. *J Neurocytol*, 20, 969-981.

Slater, C. R. (2003) Structural determinants of the reliability of synaptic transmission at the vertebrate neuromuscular junction. *J Neurocytol*, 32, 505-522.

Chamberlain, J. S., Metzger, J., Reyes, M., Townsend, D. and Faulkner, J. A. (2007) Dystrophin-deficient mdx mice display a reduced life span and are susceptible to spontaneous rhabdomyosarcoma. *Faseb J*, 21, 2195-2204.

Deconinck, A. E., Rafael, J. A., Skinner, J. A., Brown, S. C., Potter, A. C., Metzinger, L., Watt, D. J., Dickson, J. G., Tinsley, J. M. and Davies, K. E. (1997) Utrophin-dystrophin-deficient mice as a model for Duchenne muscular dystrophy. *Cell*, 90, 717-727.

Grady, R. M., Teng, H., Nichol, M. C., Cunningham, J. C., Wilkinson, R. S, and Sanes, J. R. (1997) Skeletal and cardiac myopathies in mice lacking utrophin and dystrophin: a model for Duchenne muscular dystrophy. *Cell*, 90, 729-738.

Cooper, B. J., Winand, N. J., Stedman, H., Valentine, B. A., Hoffman, E. P., Kunkel, L. M., Scott, M. O., Fischbeck, K. H., Kornegay, J. N., Avery, R. J. et al. (1988) The homologue of the Duchenne locus is defective in X-linked muscular dystrophy of dogs. *Nature*, 334, 154-156.

Partridge, T. (1997), *Models of dystrophinopathy, pathological mechanisms and assessment of therapies*. Cambridge University Press, Cambridge, pp. 310-311.

Schatzberg, S. J., Olby, N. J., Breen, M., Anderson, L. V., Langford, C. F., Dickens, H. F., Wilton, S. D., Zeiss, C. J., Binns, M. M., Kornegay, J. N. et al. (1999) Molecular analysis of a spontaneous dystrophin 'knockout' dog. *Neuromuscul Disord*, 9, 289-295.

Shimatsu, Y., Katagiri, K., Furuta, T., Nakura, M., Tanioka, Y., Yuasa, K., Tomohiro, M., Kornegay, J. N., Nonaka, I. and Takeda, S. (2003) Canine X-linked muscular dystrophy in Japan (CXMDJ). *Experimental animals/Japanese Association for Laboratory Animal Science*, 52, 93-97.

Shimatsu, Y., Yoshimura, M., Yuasa, K., Urasawa, N., Tomohiro, M., Nakura, M., Tanigawa, M., Nakamura, A. and Takeda, S. (2005) Major clinical and histopathological characteristics of canine X-linked muscular dystrophy in Japan, CXMDJ. *Acta Myol*, 24, 145-154.

Valentine, B. A., Winand, N. J., Pradhan, D., Moise, N. S., de Lahunta, A., Kornegay, J. N. and Cooper, B. J. (1992) Canine X-linked muscular dystrophy as an animal model of Duchenne muscular dystrophy: a review. *American journal of medical genetics*, 42, 352-356.

Valentine, B. A. and Cooper, B. J. (1991) Canine X-linked muscular dystrophy: selective involvement of muscles in neonatal dogs. *Neuromuscul Disord*, 1, 31-38.

Valentine, B. A., Cooper, B. J., de Lahunta, A., O'Quinn, R. and Blue, J. T. (1988) Canine X-linked muscular dystrophy. An animal model of Duchenne muscular dystrophy: clinical studies. *J Neurol Sci*, 88, 69-81.

Nguyen, F., Cherel, Y., Guigand, L., Goubault-Leroux, I. and Wyers, M. (2002) Muscle lesions associated with dystrophin deficiency in neonatal golden retriever puppies. *Journal of comparative pathology*, 126, 100-108.

Childers, M. K., Okamura, C. S., Bogan, D. J., Bogan, J. R., Petroski, G. F., McDonald, K. and Kornegay, J. N. (2002) Eccentric contraction injury in dystrophic canine muscle. *Archives of physical medicine and rehabilitation*, 83, 1572-1578.

Chetboul, V., Carlos, C., Blot, S., Thibaud, J. L., Escriou, C., Tissier, R., Retortillo, J. L. and Pouchelon, J. L. (2004) Tissue Doppler assessment of diastolic and systolic alterations of radial and longitudinal left ventricular motions in Golden Retrievers during the preclinical phase of cardiomyopathy associated with muscular dystrophy. *American journal of veterinary research*, 65, 1335-1341.

Chetboul, V., Escriou, C., Tessier, D., Richard, V., Pouchelon, J. L., Thibault, H., Lallemand, F., Thuillez, C., Blot, S, and Derumeaux, G. (2004) Tissue Doppler imaging detects early asymptomatic myocardial abnormalities in a dog model of Duchenne's cardiomyopathy. *European heart journal*, 25, 1934-1939.

Schatzberg, S. J., Anderson, L. V., Wilton, S. D., Kornegay, J. N., Mann, C. J., Solomon, G. G. and Sharp, N. J. (1998) Alternative dystrophin gene transcripts in golden retriever muscular dystrophy. *Muscle & nerve*, 21, 991-998.

Cooper, B. J., Gallagher, E. A., Smith, C. A., Valentine, B. A. and Winand, N. J. (1990) Mosaic expression of dystrophin in carriers of canine X-linked muscular dystrophy. *Laboratory investigation; a journal of technical methods and pathology*, 62, 171-178.

Banks, G. B., Gregorevic, P., Allen, J. M., Finn, E. E. and Chamberlain, J. S. (2007) Functional capacity of dystrophins carrying deletions in the N-terminal actin-binding domain. *Hum Mol Genet*, 16, 2105-2113.

Beggs, A. H., Hoffman, E. P., Snyder, J. R., Arahata, K., Specht, L., Shapiro, F., Angelini, C., Sugita, H. and Kunkel, L. M. (1991) Exploring the molecular basis for variability among patients with Becker muscular dystrophy: dystrophin gene and protein studies. *Am J Hum Genet*, 49, 54-67.

Chelly, J., Gilgenkrantz, H., Lambert, M., Hamard, G., Chafey, P., Recan, D., Katz, P., de la Chapelle, A., Koenig, M., Ginjaar, I. B. et al. (1990) Effect of dystrophin gene deletions on mRNA levels and processing in Duchenne and Becker muscular dystrophies. *Cell*, 63, 1239-1248.

Le, T. T., Nguyen, T. M., Love, D. R., Helliwell, T. R., Davies, K. E. and Morris, G. E. (1993) Monoclonal antibodies against the muscle-specific N-terminus of dystrophin: characterization of dystrophin in a muscular dystrophy patient with a frameshift deletion of exons 3-7. *Am J Hum Genet*, 53, 131-139.

Matsumura, K., Burghes, A. H., Mora, M., Tome, F. M., Morandi, L., Cornello, F., Leturcq, F., Jeanpierre, M., Kaplan, J. C., Reinert, P. et al. (1994) Immunohistochemical analysis of dystrophin-associated proteins in Becker/Duchenne muscular dystrophy with huge in-frame deletions in the NH2-terminal and rod domains of dystrophin. *The Journal of clinical investigation*, 93, 99-105.

Muntoni, F., Gobbi, P., Sewry, C., Sherratt, T., Taylor, J., Sandhu, S. K., Abbs, S., Roberts, R., Hodgson, S. V., Bobrow, M. et al. (1994) Deletions in the 5' region of dystrophin and resulting phenotypes. *Journal of medical genetics*, 31, 843-847.

Novakovic, I., Bojic, D., Todorovic, S., Apostolski, S., Lukovic, L., Stefanovic, D. and Milasin, J. (2005) Proximal dystrophin gene deletions and protein alterations in becker muscular dystrophy. *Annals of the New York Academy of Sciences*, 1048, 406-410.

Prior, T. W., Papp, A. C., Snyder, P. J., Burghes, A. H., Bartolo, C., Sedra, M. S., Western, L. M. and Mendell, J. R. (1993) A missense mutation in the dystrophin gene in a Duchenne muscular dystrophy patient. *Nature genetics*, 4, 357-360.

Takeshima, Y., Nishio, H., Narita, N., Wada, H., Ishikawa, Y., Ishikawa, Y., Minami, R., Nakamura, H. and Matsuo, M. (1994) Amino-terminal deletion of 53% of dystrophin results in an intermediate Duchenne-Becker muscular dystrophy phenotype. *Neurology*, 44, 1648-1651.

Winnard, A. V., Mendell, J. R., Prior, T. W., Florence, J. and Burghes, A. H. (1995) Frameshift deletions of exons 3-7 and revertant fibers in Duchenne muscular dystrophy: mechanisms of dystrophin production. *Am J Hum Genet*, 56, 158-166.

Warner, L. E., DelloRusso, C., Crawford, R. W., Rybakova, I. N., Patel, J. R., Ervasti, J. M. and Chamberlain, J. S. (2002) Expression of Dp260 in muscle tethers the actin cytoskeleton to the dystrophin-glycoprotein complex and partially prevents dystrophy. *Hum Mol Genet*, 11, 1095-1105.

Rybakova, I. N., Humston, J. L., Sonnemann, K. J. and Ervasti, J. M. (2006) Dystrophin and utrophin bind actin through distinct modes of contact. *The Journal of biological chemistry*, 281, 9996-10001.

The invention claimed is:

1. A method of introducing an exogenous nucleic acid into a swine cell in vitro comprising:
    exposing a first group of somatic swine cells to a transfection agent that comprises an exogenous nucleic acid during a first culture time period and
    subsequently adding a second group of somatic swine cells to the first group for a second culture time period, wherein the second group of cells have not been exposed to the transfection agent,
    wherein the first group of cells are chosen from the group consisting of primary fetal swine cells and primary swine fibroblasts.

2. The method of claim 1 wherein a ratio of the second group of cells to the first group of cells is between 1:1 and 20:1.

3. The method of claim 1 wherein the exogenous nucleic acid disrupts a target gene chosen from the group consisting of a Low-Density Lipoprotein Receptor gene (LDLR), Duchene's Muscular Dystrophy (DMD) gene, and a hairless gene (HR).

4. The method of claim 1 wherein the cells of the first group are the same cell type as the cells of the second group.

5. A method of introducing an exogenous nucleic acid into a swine cell in vitro comprising:
    exposing a first group of somatic swine cells to a transfection agent that comprises an exogenous nucleic acid during a first culture time period and
    subsequently adding a second group of somatic swine cells to the first group for a second culture time period, wherein the second group of cells have not been exposed to the transfection agent,
    wherein the cells of the first group are the same cell type as the cells of the second group.

6. The method of claim 5 wherein a ratio of the second group of cells to the first group of cells is between 1:1 and 20:1.

7. The method of claim 5 wherein the exogenous nucleic acid disrupts a target gene chosen from the group consisting of a Low-Density Lipoprotein Receptor gene (LDLR), Duchene's Muscular Dystrophy (DMD) gene, and a hairless gene (HR).

* * * * *